US006434260B1

(12) United States Patent
Soferman et al.

(10) Patent No.: US 6,434,260 B1
(45) Date of Patent: Aug. 13, 2002

(54) FACIAL IMAGING IN UTERO

(75) Inventors: Ziv Soferman, Givatayim; Michael Berman, Har Adar, both of (IL)

(73) Assignee: Biomedicom, Creative Biomedical Computing Ltd., Jerusalem (IL)

( * ) Notice: Subject to any disclaimer, the term of this patent is extended or adjusted under 35 U.S.C. 154(b) by 0 days.

(21) Appl. No.: 09/352,002

(22) Filed: Jul. 12, 1999

(51) Int. Cl.⁷ .............................. G06K 9/00; A61B 8/00
(52) U.S. Cl. ...................................... 382/131; 600/443
(58) Field of Search ............................... 382/118, 128, 382/131, 154, 285; 600/443

(56) References Cited

U.S. PATENT DOCUMENTS

| | | | |
|---|---|---|---|
| 5,239,591 A | | 8/1993 | Ranganath ...................... 382/6 |
| 5,396,890 A | * | 3/1995 | Weng ........................... 382/44 |
| 5,454,371 A | * | 10/1995 | Fenster et al. ......... 128/660.07 |
| 5,538,004 A | * | 7/1996 | Bamber ................. 128/662.06 |
| 5,706,816 A | * | 1/1998 | Mochizuki et al. ..... 128/660.07 |
| 5,754,618 A | * | 5/1998 | Okamotot et al. .......... 382/131 |
| 5,766,129 A | * | 6/1998 | Mochizuki .................. 600/443 |
| 5,954,653 A | * | 9/1999 | Hatfield et al. ............. 600/443 |
| 6,059,727 A | * | 5/2000 | Fowlkes et al. ............ 600/443 |
| 6,106,471 A | * | 8/2000 | Wiesauer et al. ........... 600/443 |
| 6,251,072 B1 | * | 6/2001 | Ladak et al. ................ 600/443 |

OTHER PUBLICATIONS

Flynn, J. et al., Surface Rendering Versus Volume Rendering In Medical Imaging: Techniques and Applications, Visualization Proceeding Nov. 1996.*

Courtney et al., "Segmentation of volume images using a multiscale transform", Proceedings of the 13th International Conference on Pattern Recognition, Aug. 1996.*

Olstad et al., "Volume rendering in medical ultrasound imaging based on nonlinear filtering", IEEE Winter workshop on Nonlinear Digital Signal Processing, Nov. 1993.*

Bohs et al., "Relative performance of two–dimensional speckle–tracking techniques: Normalized correlation, non–normalized correlation, and sum–absolute–difference", 1995 IEEE Proceedings of Ultrasonic Symposium, Nov. 1996.*

Sakas, G. et al., Visualization of 3D ultrasonic data, IEEE Proceedings Visualization '94, 1994; CP42:369–73.*

Nelson, T.R. et al., "Interactive Acquistion, Analysis, and Visualization of Sonographic Volume Data", International Journal of Imaging Systems and Technology, vol. 8:26–37, 1997.*

Nelson, T.R. et al., "Three–Dimensional Ultrasound Imaging", Ultrasound in Med & Biol., vol. 24, No. 9, pp. 1243–12709, Mar. 10, 1998.*

Volume Rendering in Medical Ultrasound Imaging Based on Nonlinear Filtering, E. Steen; B1. Olstad, The Norwegian Institute of Technology, Trondheim, Norway.

(List continued on next page.)

*Primary Examiner*—Joseph Mancuso
*Assistant Examiner*—Martin Miller
(74) *Attorney, Agent, or Firm*—Abelman, Frayne & Schwab

(57) ABSTRACT

This invention discloses a system for providing an image of at least a portion of a fetus in utero including an imager providing image data for a volume including at least a portion of a fetus in utero, an at least partially computer controlled image processing algorithm based segmenter for defining geometrical boundaries of various objects in the volume including at least a portion of a fetus in utero, and a sculpting tool, utilizing the geometrical boundaries of at least some of the various objects defined by the segmenter, for selectably removing image data relating to at least portions of the objects in order to provide a desired non-occluded image of at least a portion of the fetus in utero based on the image data.

A method for providing an image of at least a portion of a fetus in utero is also disclosed.

20 Claims, 28 Drawing Sheets

OTHER PUBLICATIONS

Product details—InViVo–ScanNT; Fraunhofer Institut fuer Graphische Datenverarbeitung IGD; Darmstadt, Germany.

Product details—3–D Ultrasound—Acquisition Methods Details, Life Imaging Systems Inc., London, Ontario, Canada.

"USCD Radiologists are Working on a New Ultrasound Technology that's Guaranteed to Produce Much Clearer Images in Three Dimensions", K. Deely; USCD Perspectives, Spring 1999.

Product details—Imaging software available from A1 Alpha Space Inc; Laguna Hills, CA, USA.

Product details—HDI1500, commercially available from Advanced Technology Laboratories; Bothell, WA, USA.

Product details—Voluson 530D, commercially available from Medison America; Pleasanton, CA, USA.

Product details—L3–Di, commercially available from Life Imaging Systems; London, Ontario, Canada.

Product details—EchoScan, Echo–View and Compact 3–D commercially available from TomTec Imaging Systems; GmbH, Unterschleissheim,. Germany.

Product details—NetralVUS, commercially available from ScImage Inc.; Los Altos, CA 94022, USA.

Product details—3–Scape, commercially available from Siemens AG; Erlangen, Germany.

Product details—Vitrea, commercially available from Vital Images Inc.; Minneapolis, MN, USA.

Product details—VoxarLib, commercially available from Voxar, Ltd.; Edinburgh, UK.

Product details—Logic 700 MR, commercially available from GE Ultrasound.

"On Active Contour Models and Balloons", L.D. Cohen, CVGIP: Image Understanding, vol. 53, No. 2, pp. 211–218 (1991).

"Finite–Element Methods for Active Contour Models and Balloons for 2–D and 3–D Images", L.D. Cohen and I. Cohen, IEEE Transactions on Pattern Analysis and Machine Intelligence, vol. 5 15, No. 11 (1993).

"Snakes, Active Contours, and Deformable Models", http://www.wpi.edu/~dima/ummed/presentation/index.html.

* cited by examiner

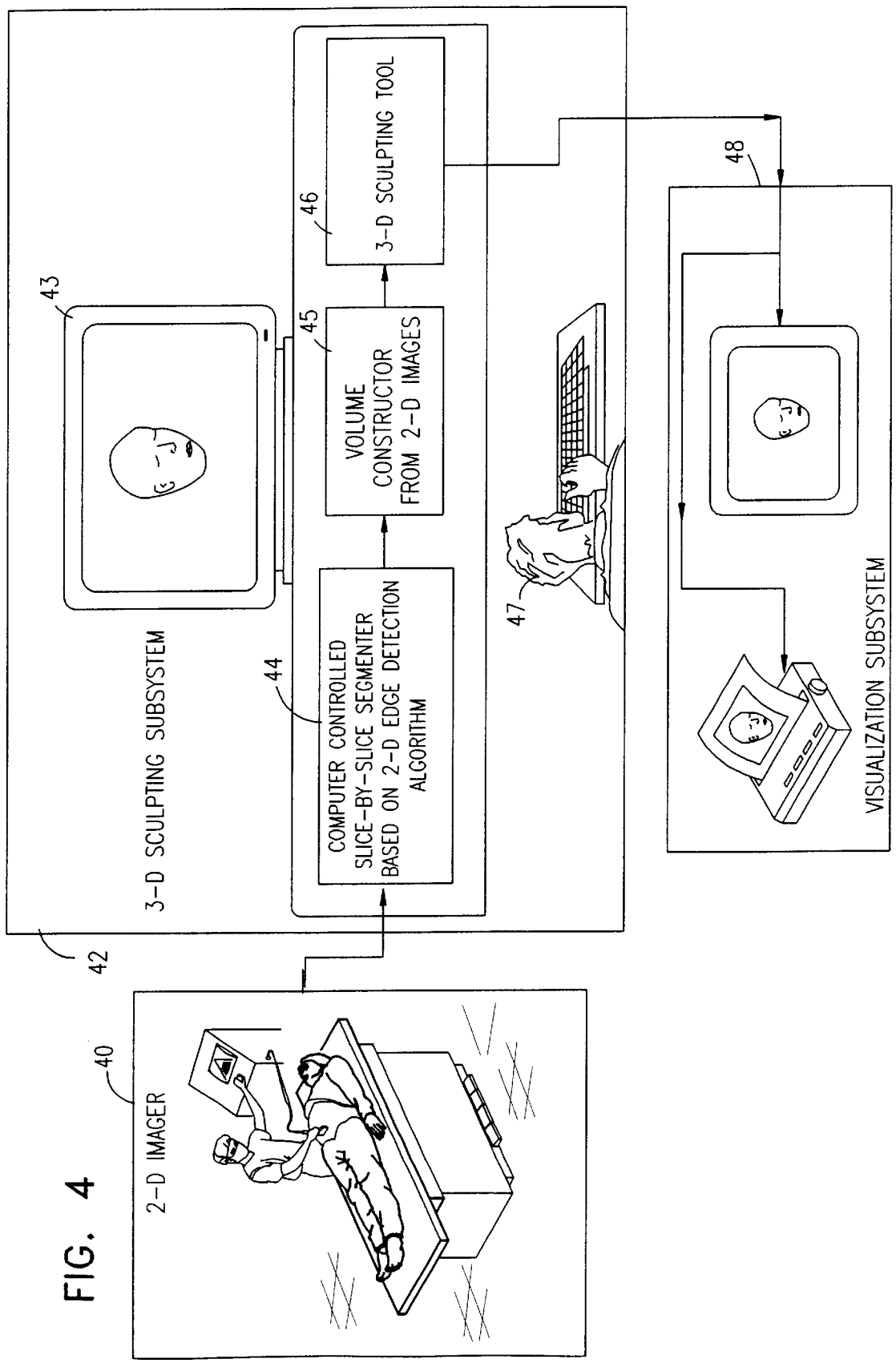

DEFINE $\phi, \theta$ AS THE ORIENTATION OF THE FILTERING OPERATOR AXIS RELATIVE TO THE VOLUME IMAGE SYSTEM OF AXES: LET $\phi$ BE THE ELEVATION ANGLE OF THE AXIS RELATIVE TO THE XY PLANE, AND $\theta$ THE ANGLE BETWEEN THE PROJECTED OPERATOR AXIS ON THE XY PLANE AND THE X DIRECTION. DISCRETIZE THE OPERATOR ORIENTATION ANGLES SO THAT:

$$\theta = k\Delta\theta, \Delta\theta = \pi/K, k = 0,1,2,3,...K-1; \phi = s\Delta\phi, \Delta\phi = \pi/2S, s = 0,1,2,3,...S$$

(TYPICALLY K=36, S=9).

DEFINE:

FOR EACH VOXEL POSITIONED AT $\underline{X}_0 = (x_0, y_0, z_0)$ (IN THE VOLUME IMAGE COORDINATES) IN THE REGION OF INTEREST, CALCULATE THE DISCRETE CONVOLUTION/CORRELATION WITH THE ENHANCEMENT OPERATOR IN THE FOLLOWING WAY:

DEFINE X,Y,Z AS THE AXES OF THE VOLUMETRIC IMAGE COORDINATE SYSTEM.. DEFINE $\underline{I}, \underline{J}, \underline{K}$ TO BE 3 UNIT VECTORS IN THE MAIN DIRECTIONS IN THE OPERATOR'S SYSTEM OF AXES, AS SEEN IN FIG. 10: $\underline{K}$ IS A UNIT VECTOR ALONG THE OPERATOR'S SYMMETRY AXIS, $\underline{I}$ IS ORTHOGONAL TO $\underline{K}$ AND IS PARALLEL TO THE XY PLANE. (IF $\underline{K}$ IS PARALLEL TO THE Z DIRECTION OF THE VOLUME IMAGE SYSTEM- CHOOSE $\underline{I}$ TO BE ORTHOGONAL TO $\underline{K}$ AND TO THE X AXIS). CHOOSE $\underline{J}$ TO BE ORTHOGONAL BOTH TO $\underline{K}$ AND TO $\underline{I}$. MORE SPECIFICALLY, THE UNIT VECTORS IN TERMS OF THE X,Y,Z COORDINATE SYSTEM:

$\underline{K} = (cos(\phi)cos(\theta), cos(\phi)sin(\theta), sin(\phi))$ $\underline{I} = (sin(\theta), -cos(\theta), 0)$ $\underline{J} = (-sin(\phi)cos(\theta), -sin(\phi)sin(\theta), cos(\phi))$ DEFINE $\underline{X}_0 = (x_0, y_0, z_0)$ TO BE THE POSITION VECTOR OF THE OPERATOR'S CENTER IN THE X,Y,Z SYSTEM OF COORDINATES (CENTERED AT THE VOXEL OF THE SAME COORDINATES). A POINT WHOSE COORDINATES ARE (i,j,k) IN THE OPERATOR SYSTEM OF AXES, HAS THE COORDINATES $\underline{X}(i,j,k) = \underline{X}_0 + i\underline{I} + j\underline{J} + K\underline{k}$ (IN VECTOR NOTATION) IN THE X,Y,Z SYSTEM OF AXES.

DEFINE THE AVERAGE $\alpha$ OF THE IMAGE WITHIN A FILLED CIRCLE OF RADIUS R CENTERED AT $\underline{X}_0$ AND PERPENDICULAR TO THE OPERATOR AXIS AS FOLLOWS:

$$a(\underline{X}_0, \phi, \theta, R) = \frac{1}{Ninside} \sum_{i,j \in C} Vol\_Image[\underline{X}(i,j,0)]$$

WHERE: $C$ IS THE SET OF ALL $(i,j)$ SUCH THAT $i^2 + j^2 \leq R^2$, $Ninside$ IS THE NUMBER OF SUCH $(i,j)$'s WITHIN $C$, AND Vol_Image[$\underline{X}(i,j,0)$] IS THE VALUE OF THE VOXEL POSITIONED AT $\underline{X}(i,j,0)$ IN THE VOLUME IMAGE SYSTEM OF AXES.

FIG. 9A

FOR EACH ORIENTATION $\theta$ RELATIVE TO THE HORIZONTAL AXIS (X) OF THE IMAGE WHERE: $\theta = k\Delta\theta, \Delta\theta = \pi/K$, $k = 0,1,2,3,...K-1$, (TYPICALLY K=36) DEFINE:

FOR EACH PIXEL IN THE REGION OF INTEREST CALCULATE THE DISCRETE AVERAGE 'a' ALONG A LINE OF LENGTH L ORIENTED AT AN ANGLE $\theta$ AND CENTERED AT THE PIXEL WITH INTEGER COORDINATES (x0,y0) AS SEEN IN FIG. 17 IN THE FOLLOWING WAY:

$$a(x0, y0, \theta, L) = \frac{1}{N+1} \sum_{m=-N/2}^{+N/2} \text{Image}(x0 + m\Delta x, y0 + m\Delta y)$$

where $$\Delta x = \frac{L}{N}\cos(\theta); \Delta y = \frac{L}{N}\sin(\theta)$$

L IS THE LENGTH OF THE LINE IN PIXELS, N+1 IS THE NUMBER OF SAMPLING POINTS ALONG THE LINE. N HAS TO BE AN EVEN NUMBER, TYPICALLY LARGER THAN 2L. Image$(x0 + m\Delta x, y0 + m\Delta y)$ IS THE IMAGE VALUE AT $(x0 + m\Delta x, y0 + m\Delta y)$. IF THE COORDINATES $(x0 + m\Delta x, y0 + m\Delta y)$ ARE NON-INTEGERS, THE IMAGE VALUE AT $(x0 + m\Delta x, y0 + m\Delta y)$ IS OBTAINED BY BILINEAR INTERPOLATION FROM THE IMAGE VALUES AT NEIGHBORING PIXELS WITH INTEGER COORDINATES.

---

FOR EACH PIXEL IN THE REGION OF INTEREST USE THE ABOVE AVERAGE TO PRODUCE THE DIRECTIONAL DERIVATIVE $h'$ BY SUBTRACTING FROM THE AVERAGE 'a' ALONG THE LINE CENTERED AT THE PIXEL, HALF OF THE AVERAGES ALONG PARALLEL LINES, NAMELY CALCULATE:

$$h'(x0, y0, \theta, D, L) = a(x0, y0, \theta, L) - 0.5 \cdot (a(x1, y1, \theta, L) + a(x2, y2, \theta, L))$$

where:

$$x1 = x0 + D \cdot COS(\theta + \pi/2); y1 = y0 + D \cdot SIN(\theta + \pi/2)$$
$$x2 = x0 + D \cdot COS(\theta - \pi/2); y2 = y0 + D \cdot SIN(\theta - \pi/2)$$

IN WHICH D IS THE DISTANCE BETWEEN THE CENTRAL LINE AND THE TWO PARALLEL SIDE LINES.

IN PRACTICE $a(x1, y1, \theta, L), a(x2, y2, \theta, L))$ ARE OBTAINED BY BILINEAR INTERPOLATION FROM THE VALUES OF THE AVERAGE $a(i, j, \theta, L)$ AT NEIGHBORING INTEGER COORDINATES.

FIG. 13A

FOR EACH PIXEL IN THE REGION OF INTEREST FIND THE MAXIMAL VALUE OF $-h'(x0, y0, k \cdot \Delta\theta, D, L)$ FOR $k$=0,1,2,...,K-1, AND $\Delta\theta = \pi/K$. TYPICALLY K=36. IF THE MAXIMUM ASSOCIATED WITH A CERTAIN PIXEL IS LOWER THAN ZERO THEN SET IT TO ZERO. NAMELY, $$h(x0, y0, D, L) \stackrel{def}{=} MAX\{0, \underset{0 \leq k \leq K-1}{MAX}\{-h'(x0, y0, k \cdot \Delta\theta, D, L)\}\}$$

DEFINE THE EDGE ENHANCED IMAGE AT THE PIXEL (x0,y0) TO BE THE VALUE OF $h(x0,y0,D,L)$ FOR (x0,y0) IN THE REGION OF INTEREST, AND ZERO ELSEWHERE. THE RESULT IS A NEW IMAGE WHICH IS THE EDGE ENHANCED IMAGE. THE PARAMETERS D AND L ARE OPTIMIZED THROUGH EXPERIENCE.

OUTPUT EDGE ENHANCED IMAGE

FIG. 13B

AS SEEN IN FIG. 18B, TO EACH SUCH CONNECTING SEGMENT ASSOCIATE A WEIGHT ACCORDING TO: (1) ITS PROXIMITY TO THE INITIAL MARKING (2) THE DEGREE OF SIMILARITY OF THE CONNECTING SEGMENT DIRECTION TO THE CORRESPONDING DIRECTION OF THE INITIAL MARKINGS AT THAT LOCATION, (3) THE AVERAGE INTENSITY OF THE EDGE ENHANCED IMAGE ALONG THE CONNECTING SEGMENT, AND (4) OPTIONALLY INTRODUCE AN INPUT WEIGHT FROM PREVIOUS OR OTHER SLICE/S.. AN EXAMPLE OF THE FORMULA USED IN THE PREFERRED EMBODIMENT:

DEFINE THE WEIGHTING FUNCTIONS $W^t_{ij}$ TO BE THE WEIGHT ASSOCIATED WITH THE SEGMENT CONNECTING DISCRETIZATION POINT $i$ IN NORMAL $t$ TO DISCRETIZATION POINT $j$ IN NORMAL $t+1$.

$$W^t_{ij} = -\alpha W^t_{1ij} + \beta W^t_{2ij} + \gamma W^t_{3ij} + \delta W^t_{4ij}$$

WHERE:

$W^t_{1ij}$ = AVERAGE OF VALUES IN THE ARRAY h(i,j,D,L) (THE EDGE ENHANCED IMAGE ARRAY) ALONG THE CONNECTING SEGMENT FROM POINT i ON NORMAL t TO POINT j ON NORMAL t+1. $\alpha, \beta, \gamma, \delta$ ARE WEIGHTING FACTORS OPTIMIZED THROUGH EXPERIENCE.

IN THIS SPECIFIC EXAMPLE, ALL NORMALS ARE DISCRETIZED INTO 2U+1 EQUALLY SPACED POINTS.    $-U \le i \le U$;  $-U \le j \le U$    AND THE NORMAL INTERSECTS THE INITIAL MARKING FOR i=j=0 AND ALL NORMALS ARE OF THE SAME LENGTH.

$W^t_{2ij}$ = |i-j|/2U APPROXIMATING THE DEGREE OF SIMILARITY OF THE DIRECTION OF THE CONNECTING SEGMENT TO THE CORRESPONDING DIRECTION OF THE INITIAL MARKING AT THAT LOCATION.

$W^t_{3ij}$ = (i+j)/2U THE PROXIMITY OF THE CONNECTING SEGMENT TO THE INITIAL MARKING.

$W^t_{4ij}$ =    OPTIONAL: INPUT WEIGHT TERM FROM OTHER SLICE/S

FIG. 14B

FACIAL IMAGING IN UTERO

FIELD OF THE INVENTION

The present invention relates to facial imaging generally and more particularly to facial imaging in utero.

BACKGROUND OF THE INVENTION

Various techniques are known for facial imaging in utero using ultrasonic technology. The quality and completeness of such images is generally rather non-uniform and depends inter alia on the position of the face of a fetus relative to ultra-sound imaging apparatus. Conventional systems which provide facial imaging in utero are known inter alia from the following publications:

U.S. Pat. No. 5,239,591;

InViVo-ScanNT of the Fraunhofer Institut fuer Graphische Datenverarbeitung IGD in Darmstadt, Germany, commercially available;

3-D Ultrasound—Acquisition Methods Details, of Life Imaging Systems, Inc. of London, Ontario UCSD radiologists are working on a new ultrasound technology that's guaranteed to produce much clearer images in three dimensions. by Kate Deely, UCSD Perspectives, Spring 1999;

Product literature relating to the following products:

Imaging software available from A1 Alpha Space, Inc, of Laguna Hills, Calif., U.S.A. and from Echotech 3-D of Hallbergmoos, Germany;

HDI1500 commercially available from ATL—Advanced Technology Laboratories, Bothell, Wash., U.S.A.;

Voluson 530D commercially available from Kretztechnik AG of Zipf, Austria and from Medison America of Pleasanton, Calif., U.S.A. This ultrasound system includes a scalpel feature which enables manual removal of occlusions blocking full visualization of a fetal face.

L3-Di commercially available from Life Imaging Systems Inc. of London, Ontario, Canada;

Echo-Scan, Echo-View and Compact3-D commercially available from TomTec Imaging Systems GmbH of Unterschleissheim, Germany;

NetralVUS, commercially available from ScImage, Inc. of Los Altos, Calif. 94022, U.S.A.;

3-Scape commercially available from Siemens AG of Erlangen, Germany;

Vitrea, commercially available from Vital Images, Inc of Minneapolis, Minn., U.S.A.;

VoxarLib, commercially available from Voxar Ltd. of Edinburgh, UK;

LOGIC 700 MR commercially available from GE Ultrasound.

SUMMARY OF THE INVENTION

The present invention seeks to provide an improved system for fetal face imaging in utero.

There is thus provided in accordance with a preferred embodiment of the present invention a system for providing an image of at least a portion of a fetus in utero including an imager providing image data for a volume including at least a portion of a fetus in utero, an at least partially computer controlled image processing algorithm based segmenter for defining geometrical boundaries of various objects in the volume including at least a portion of a fetus in utero, and a sculpting tool, utilizing the geometrical boundaries of at least some of the various objects defined by the segmenter, for selectably removing at least portions of the objects in order to provide a desired non-occluded image of at least a portion of the fetus in utero, based on the image data.

Further in accordance with a preferred embodiment of the present invention the imager is an ultrasound imager.

Still further in accordance with a preferred embodiment of the present invention the image data contains speckles.

Preferably the segmenter is fully automatic. Alternatively the segmenter is semi-automatic.

Additionally in accordance with a preferred embodiment of the present invention the segmenter operates substantially in real time.

Further in accordance with a preferred embodiment of the present invention the segmenter defines geometrical boundaries in at least one slice of the volume by employing previously acquired information relating to at least another slice of the volume.

Preferably the segmenter operates in a slice-by-slice manner.

There is also provided in accordance with a preferred embodiment of the present invention a method for providing an image of at least a portion of a fetus in utero, the method including providing image data for a volume including at least a portion of a fetus in utero, utilizing an at least partially computer controlled image processing algorithm based segmenter to define geometrical boundaries of various objects in the volume including at least a portion of a fetus in utero, and utilizing the geometrical boundaries of at least some of said various objects defined by the segmenter to selectably remove image data relating to at least portions of the objects in order to provide a desired non-occluded image of at least a portion of the fetus in utero, based on the image data.

Further in accordance with a preferred embedment of the present invention the method employs ultrasound.

Additionally in accordance with a preferred embodiment of the present invention, the image data contains speckles.

Still further in accordance with a preferred embodiment of the present invention the segmenter operates fully automatically. Alternatively the segmenter operates semi-automatically.

Moreover in accordance with a preferred embodiment of the present invention the segmenter operates substantially in real time.

Additionally in accordance with a preferred embodiment of the present invention the segmenter defines geometrical boundaries in at least one slice of the volume by employing previously acquired information relating to at least another slice of the volume.

Still further in accordance with a preferred embodiment of the present invention the segmenter operates in a slice-by-slice manner.

BRIEF DESCRIPTION OF THE DRAWINGS

The present invention will be understood and appreciated more fully from the following detailed description, taken in conjunction with the drawings in which:

FIG. 4 is a simplified block diagram illustration of a fetal face imaging system constructed and operative in accordance with still another preferred embodiment of the present invention employing a 2-D imager and a 2-D slice-by-slice segmenter followed immediately by a volume constructor, followed by 3-D sculpting and visualization tools;

FIGS. 9A and 9B together are a flowchart illustrating a three-dimensional filtering operation performed in accordance with a preferred embodiment of the present invention on an original volume image;

FIGS. 13A and 13B together are a flowchart illustrating a two-dimensional filtering operation performed in accordance with a preferred embodiment of the present invention on an original volume image;

FIGS. 14A and 14B together are a flow chart illustrating one part of an optimal boundary defining step of the operation of FIG. 11 in accordance with a preferred embodiment of the present invention;

DETAILED DESCRIPTION OF PREFERRED EMBODIMENTS

Figure 1:
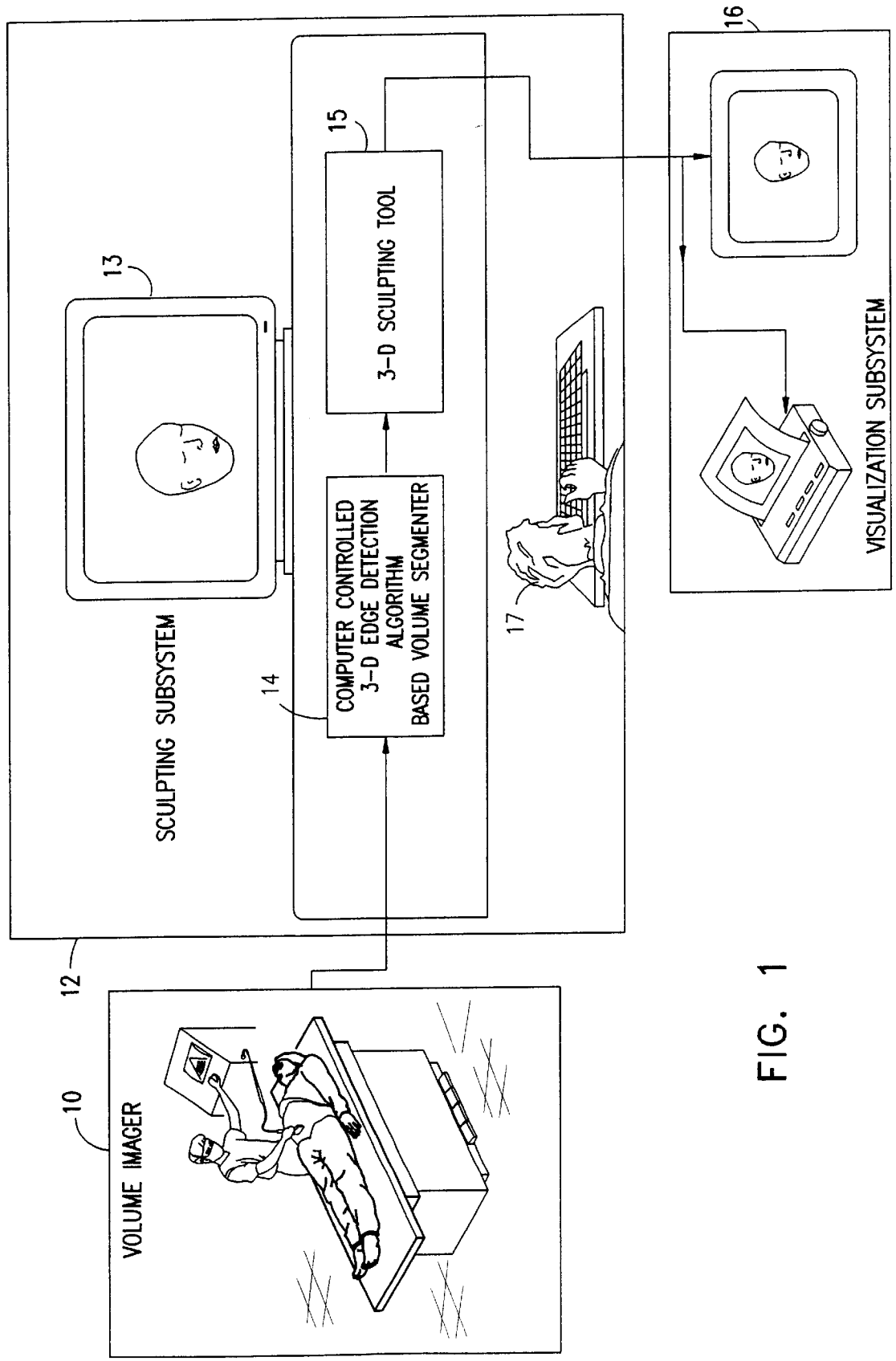
FIG. 1 is a simplified block diagram illustration of a fetal face imaging system constructed and operative in accordance with a preferred embodiment of the present invention and employing a volume imager and a volume segmenter followed by sculpting and visualization tools.

Reference is now made to FIG. 1, which is a simplified block diagram illustration of a fetal face imaging system constructed and operative in. accordance with a preferred embodiment of the present invention.

As seen in FIG. 1, the fetal face imaging system of one embodiment of the present invention preferably comprises a volume imager 10. Volume imager 10 may be of any suitable type and may employ any suitable technology, such as, for example, ultrasound imaging. It is also possible that magnetic resonance imaging (MRI) could be employed. Currently available ultrasound volume imagers and imaging software include:

Imaging software available from A1 Alpha Space, Inc, of Laguna Hills, Calif., U.S.A. and from Echotech 3-D of Hallbergmoos, Germany;

HDI1500 commercially available from ATL—Advanced Technology Laboratories, Bothell, Wash., U.S.A.;

Voluson 530D commercially available from Kretztechnik AG of Zipf, Austria and from Medison America of Pleasanton, Calif., U.S.A.

L3-Di commercially available from Life Imaging Systems Inc. of London, Ontario, Canada;

Echo-Scan, Echo-View and Compact3-D commercially available from TomTec Imaging Systems GmbH of Unterschleissheim, Germany;

NetralVUS, commercially available from ScImage, Inc. of Los Altos, Calif. 94022, U.S.A.;

3-Scape commercially available from Siemens AG of Erlangen, Germany;

Vitrea, commercially available from Vital Images, Inc of Minneapolis, Minn., U.S.A.;

VoxarLib, commercially available from Voxar Ltd. of Edinburgh, UK;

Conventional 2-D ultrasound images are also available from the following sources: ATL—Advanced Technology Laboratories, Bothell, Wash., U.S.A., Siemens AG, Acuson Corporation of Mountain View, Calif., U.S.A., GE Medical Systems of Milwaukee, Wis., U.S.A., Toshiba America Medical Systems of Tustin, Calif., U.S.A. and Hewlett-Packard Medical Group of Palo Alto, Calif.

It is appreciated that most currently available volume imagers operate on a slice-by-slice basis. It is anticipated, however, that volume imagers which do not operate on a slice-by-slice basis will become available in the future and will also be useful in the present invention.

In accordance with a preferred embodiment of the present invention, image data from volume imager 10 is supplied to a sculpting subsystem 12 preferably embodied in a workstation 13 including a computer controlled image processing algorithm based volume segmenter, preferably a computer controlled 3-D edge detection algorithm based volume segmenter 14. The volume imager 10 provides a volume image which may be acquired directly or by acquiring a series of 2-D images and construction a volume image therefrom. Typically segmenter 14 receives the output of volume imager 10 in 3-D form and enables a workstation operator 17 using that output, to readily locate and isolate a fetal face image and, as necessary to remove parts of the image which occlude a full view of the fetal face from a desired perspective.

Segmenter 14, as will be described hereinbelow in detail, is operative in a computer-assisted manner, preferably under the control of the operator 17, to differentiate between various body parts and to distinguish the fetus or the fetal face from its environment, such as for example, from the amniotic fluid in which it resides and the surrounding placenta and uterus.

Preferably modified or annotated image data from segmenter 14 is employed by a 3-D sculpting tool 15. It is appreciated that sculpting tool 15 may be used not only to remove occlusions but also to otherwise enhance the fetal face image. It is additionally appreciated that there may be cases where operator input in the operation of sculpting tool 15 may be unnecessary. In such a case, the sculpting tool 15 may be entirely computer controlled and operated.

It is appreciated that sculpting subsystem 12 may be integrated in the same computer platform which serves to control the operation of volume imager 10.

The output of sculpting subsystem 12, typically in the form of modified or annotated image data, is preferably supplied to a visualization subsystem 16, which may comprise, for example, a video display, a video recorder or transmitter, or a printer or even a three dimensional model generator. It is appreciated that the visualization subsystem may include image processing circuitry and software for desired image enhancement or modification.

Figure 2:
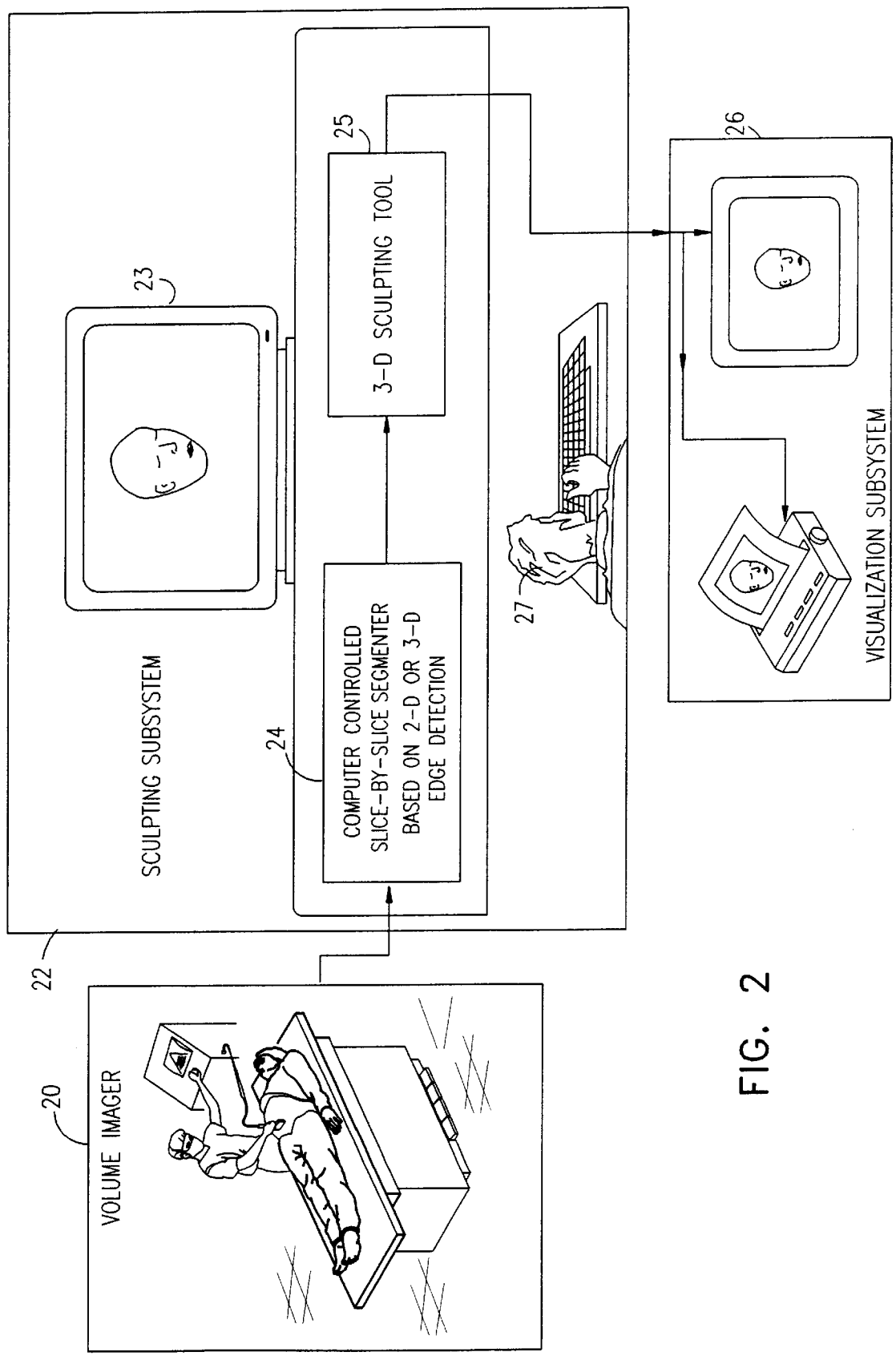
FIG. 2 is a simplified block diagram illustration of a fetal face imaging system constructed and operative in accordance with another preferred embodiment of the present invention employing a volume imager and a slice-by-slice volume segmenter followed by sculpting and visualization tools.

Reference is now made to FIG. 2, which is a simplified block diagram illustration of a fetal face imaging system constructed and operative in accordance with another preferred embodiment of the present invention.

As seen in FIG. 2, the fetal face imaging system of another embodiment of the present invention preferably comprises a volume imager 20. Volume imager 20 may be of any suitable type and may employ any suitable technology, such as, for example, ultrasound and magnetic resonance imaging (MRI). Currently available volume imagers include products listed hereinabove with reference to FIG. 1.

In accordance with a preferred embodiment of the present invention, image data from volume imager 20 is supplied to a sculpting subsystem 22 preferably embodied in a workstation 23 including a computer controlled image processing algorithm based slice-by-slice segmenter, preferably a computer controlled slice-by-slice segmenter based on 2-D or 3-D edge detection 24. Typically segmenter 24 receives the output of volume imager 20 in either 2-D or 3-D form and enables a workstation operator 27, using that output, to readily locate and isolate a fetal face image and, as necessary to remove parts of the image which occlude a full view of the fetal face from a desired perspective.

Segmenter 24, as will be described hereinbelow in detail, is operative slice-by-slice in a computer-assisted manner, preferably under the control of the operator 27, to differentiate between various body parts and to distinguish the fetus or the fetal face from its environment, such as for example, from the amniotic fluid in which it resides and the surrounding placenta and uterus.

Preferably modified or annotated image data from segmenter 24 is employed by a 3-D sculpting tool 25. It is appreciated that sculpting tool 25 may be used not only to remove occlusions but also to otherwise enhance the fetal face image. It is additionally appreciated that there may be cases where operator input in the operation of sculpting tool 25 may be unnecessary. In such a case, the sculpting tool 25 may be entirely computer controlled and operated.

It is appreciated that sculpting subsystem 22 may be integrated in the same computer platform which serves to control the operation of volume imager 20.

The output of sculpting subsystem 22, typically in the form of modified or annotated image data, is preferably supplied to a visualization subsystem 26, which may comprise, for example, a video display, a video recorder or transmitter, or a printer or even a three dimensional model generator. It is appreciated that the visualization subsystem may include image processing circuitry and software for desired image enhancement or modification.

Figure 3:
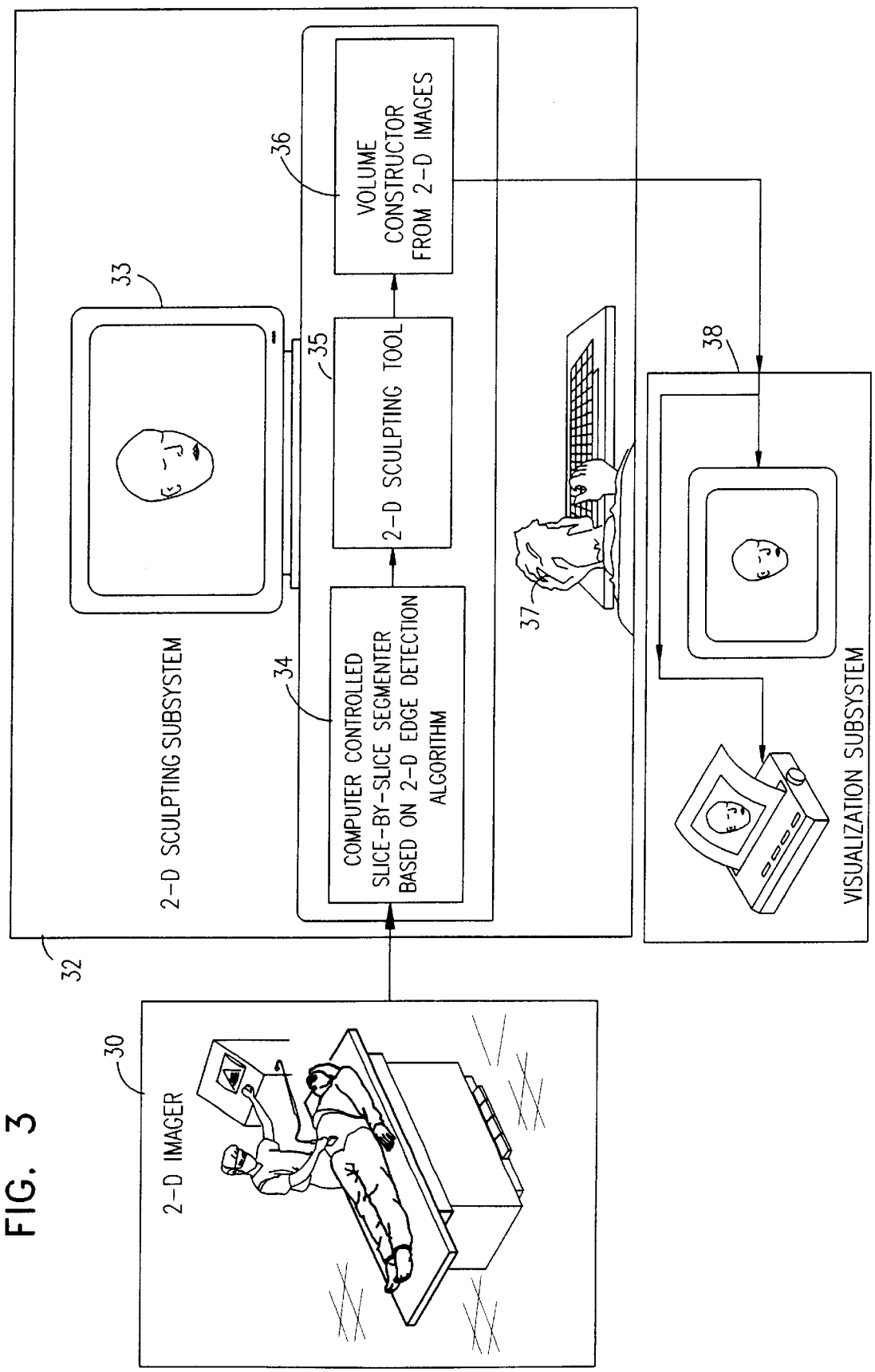
FIG. 3 is a simplified block diagram illustration of a fetal face imaging system constructed and operative in accordance with yet another preferred embodiment of the present invention it employing a 2-D imager, a 2-D slice-by-slice segmenter and a 2-D sculpting tool followed by a volume constructor and a visualization subsystem.

Reference is now made to FIG. 3, which is a simplified block diagram illustration of a fetal face imaging system constructed and operative in accordance with yet another preferred embodiment of the present invention.

As seen in FIG. 3, the fetal face imaging system preferably comprises a two-dimensional (2-D) imager 30. Two-dimensional imager 30 may be of any suitable type and may employ any suitable technology, such as, for example, ultrasound. Currently available 2-D imagers are listed hereinabove with reference to FIG. 1.

In accordance with a preferred embodiment of the present invention, image data from 2-D imager 30 is supplied to a 2-D sculpting subsystem 32 preferably embodied in a workstation 33 including a computer controlled 2-D image processing algorithm based segmenter, preferably a computer controlled slice-by-slice segmenter based on a 2-D edge detection algorithm 34. Typically segmenter 34 receives the output of 2-D imager 30 in 2-D form and makes it possible, with or without operator (37) intervention, to readily locate and isolate a fetal face image and, as necessary, to remove parts of the image which occlude a full view of the fetal face from a desired perspective.

Segmenter 34, as will be described hereinbelow in detail, is operative slice-by-slice in a computer-assisted manner, preferably under the control of an operator 37, to differentiate between various body parts and to distinguish the fetus or the fetal face from its environment, such as for example, from the amniotic fluid in which it resides and the surrounding placenta and uterus.

Preferably modified or annotated image data from segmenter 34 is employed by a 2-D sculpting tool 35. It is appreciated that sculpting tool 35 may be used not only to remove occlusions but also to otherwise enhance the fetal face image. It is additionally appreciated that there may be cases where operator input in the operation of sculpting tool 35 may be unnecessary. In such a case, the sculpting tool 35 may be entirely computer controlled and operated.

The output of sculpting tool 35 is preferably supplied to a volume constructor 36 which is operative to construct a volume image from a plurality of individual slices of two-dimensional image data, while preserving the segmentation and sculpting thereof.

It is appreciated that sculpting subsystem 32 may be integrated in the same computer platform which serves to control the operation of 2-D imager 30.

The output of sculpting subsystem 32, typically in the form of modified or annotated image data, is preferably supplied to a visualization subsystem 38, which may comprise, for example, a video display, a video recorder or transmitter, or a printer or even a three dimensional model generator. It is appreciated that the visualization subsystem may include image processing circuitry and software for desired image enhancement or modification.

Reference is now made to FIG. 4, which is a simplified block diagram illustration of a fetal face imaging system constructed and operative in accordance with yet another preferred embodiment of the present invention.

As seen in FIG. 4, the fetal face imaging system of yet another embodiment of the present invention preferably comprises a two-dimensional (2-D) imager 40. Two-dimensional imager 40 may be of any suitable type and may employ any suitable technology, such as, for example, ultrasound. Currently available 2-D imagers are listed hereinabove, with reference to FIG. 1.

In accordance with a preferred embodiment of the present invention, image data from 2-D imager 40 is supplied to a sculpting subsystem 42 preferably embodied in a workstation 43 including a computer controlled 2-D image processing algorithm based segmenter, preferably a computer controlled slice-by-slice segmenter based on a 2-D edge detection algorithm 44. Typically segmenter 44 receives the output of 2-D imager 40 in 2-D form and makes it possible to readily locate and isolate a fetal face image and, as necessary, to remove parts of the image which occlude a full view of the fetal face from a desired perspective.

Segmenter 44, as will be described hereinbelow in detail, is operative slice-by-slice in a computer-assisted manner, preferably under the control of an operator 47, to differentiate between various body parts and to distinguish the fetus or the fetal face from its environment, such as for example, from the amniotic fluid in which it resides and the surrounding placenta and uterus.

Preferably modified or annotated image data from segmenter 44 supplied to a volume constructor 45, which is operative to construct a volume image from a plurality of individual slices of two-dimensional image data, while preserving the segmentation thereof.

The output of volume constructor 45 is preferably supplied to a 3-D sculpting tool 46. It is appreciated that 3-D sculpting tool 46 may be used not only to remove occlusions but also to otherwise enhance the fetal face image. It is additionally appreciated that there may be cases where operator input in the sculpting tool 46 may be unnecessary or obviated by operation of the segmenter 44. In such a case, the sculpting tool 46 may be entirely computer controlled and operated.

It is appreciated that sculpting subsystem 42 may be integrated in the same computer platform which serves to control the operation of 2-D imager 40.

The output of sculpting subsystem 42, typically in the form of modified or annotated image data, is preferably supplied to a visualization subsystem 48, which may comprise, for example, a video display, a video recorder or transmitter, or a printer or even a three dimensional model generator. It is appreciated that the visualization subsystem may include image processing circuitry and software for desired image enhancement or modification.

Figure 5A:
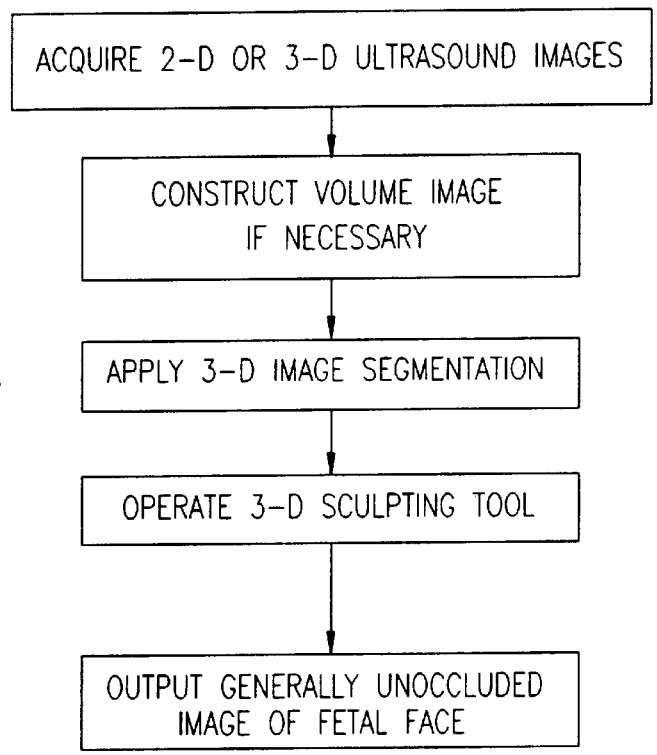
FIG. 5A is a flow chart illustrating operation of the system of FIG. 1 in accordance with a preferred embodiment of the present invention.

Reference is now made to FIG. 5A, which is a flow chart illustrating operation of the system of FIG. 1 in accordance with a preferred embodiment of the present invention. As seen in FIG. 5A, a series of 2-D ultrasound images or a 3-D ultrasound image may be acquired by volume imager 10 (FIG. 1). The relationship of the 2-D ultrasound images is preferably one of adjacent slices of a volume image, such that a volume image is constructed therefrom. Alternatively, where possible, a 3-D volume image may be acquired directly.

The operation of segmenter 14 of sculpting subsystem 12 (FIG. 1) is to apply computer-assisted or computer-controlled 3-D image segmentation with a view towards isolating an image of a fetal face from the volume image data received from the volume imager 10 (FIG. 1).

Following 3-D image segmentation, sculpting tool 15 (FIG. 1) is operative, normally, but not necessarily, without operator intervention, to eliminate portions of the isolated image which occlude a desired image of a fetal face. Following operation of sculpting subsystem 12, a generally unoccluded image of the fetal face, with or without further image enhancement, is produced.

Figure 5B:
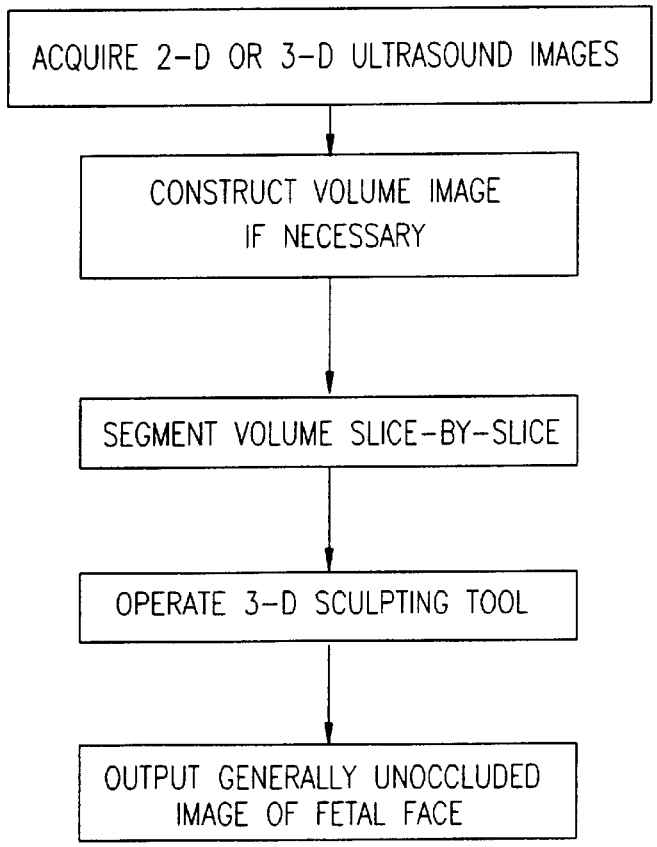
FIG. 5B is a flow chart illustrating operation of the system of FIG. 2 in accordance with a preferred embodiment of the present invention.

Reference is now made to FIG. 5B, which is a flow chart illustrating operation of the system of FIG. 2 in accordance with another preferred embodiment of the present invention. As seen in FIG. 5B, a series of 2-D ultrasound images may be acquired by volume imager 20 (FIG. 2). The relationship of the 2-D ultrasound images is preferably one of adjacent slices of a volume image, such that a volume image is constructed therefrom. Alternatively, where possible, a 3-D volume image may be acquired directly.

In this embodiment, the volume image may be converted into a series of 2-D image slices. These slices may correspond to the 2-D image slices originally acquired or alternatively may be sliced in different planes.

The operation of segmenter 24 of sculpting subsystem 22 (FIG. 2) in this embodiment is to apply computer-assisted or computer-controlled image segmentation on a slice-by-slice basis with a view towards isolating an image of a fetal face from the volume image data received from the volume imager 20 (FIG. 2).

Following image segmentation, 3-D sculpting tool 25 (FIG. 2) is operative normally, but not necessarily, without operator intervention, to eliminate portions of the isolated image which occlude a desired image of a fetal face. Following operation of sculpting subsystem 22, a generally unoccluded image of the fetal face, with or without further image enhancement, is produced.

Figure 5C:
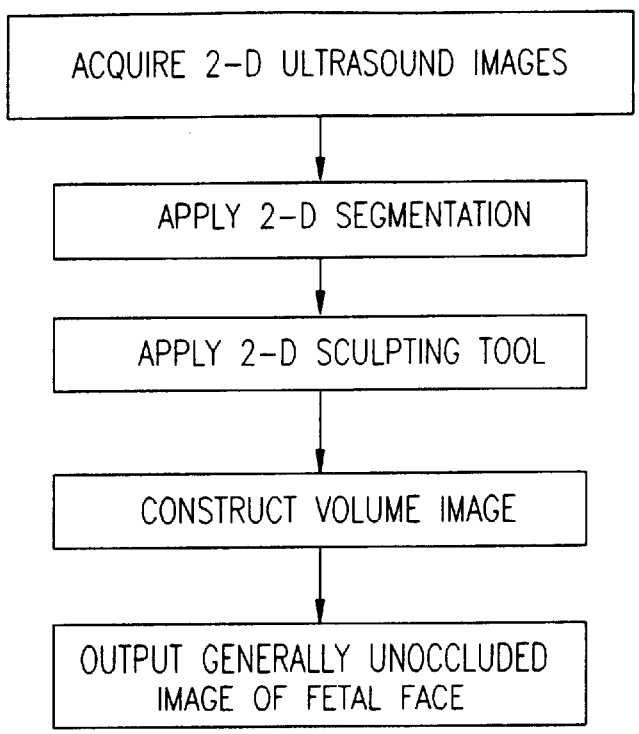
FIG. 5C is a flow chart illustrating operation of the system of FIG. 3 in accordance with a preferred embodiment of the present invention.

Reference is now made to FIG. 5C, which is a flow chart illustrating operation of the system of FIG. 3 in accordance with another preferred embodiment of the present invention. As seen in FIG. 5C, a series of 2-D ultrasound images may be acquired by 2-D imager 30 (FIG. 3). The relationship of the 2-D ultrasound images is preferably one of adjacent slices of a volume image, such that a volume image is constructed therefrom.

The operation of segmenter 34 of sculpting subsystem 32 (FIG. 3) in this embodiment is to apply computer-assisted or computer-controlled image segmentation on a slice-by-slice basis with a view towards isolating an image of a fetal face from the volume image data received from the 2-D imager 30 (FIG. 3).

Following image segmentation, 2-D sculpting tool 35 (FIG. 3) is operative normally, but not necessarily, without operator intervention, to eliminate portions of the isolated image which occlude a desired image of a fetal face. Following operation of sculpting subsystem 32 and volume constructor 36 (FIG. 3) a generally unoccluded image of the fetal face, with or without further image enhancement, is produced.

Figure 5D:
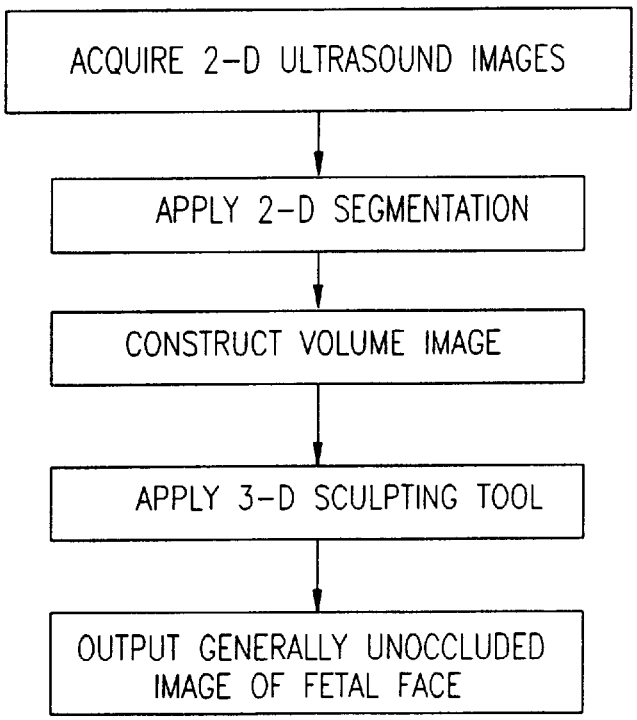
FIG. 5D is a flow chart illustrating operation of the system of FIG. 4 in accordance with a preferred embodiment of the present invention.

Reference is now made to FIG. 5D, which is a flow chart illustrating operation of the system of FIG. 4 in accordance with another preferred embodiment of the present invention. As seen in FIG. 5D, a series of 2-D ultrasound images may be acquired by 2-D imager 40 (FIG. 4). The relationship of the 2-D ultrasound images is preferably one of adjacent slices of a volume image, such that a volume image is constructed therefrom.

The operation of segmenter 44 of sculpting subsystem 42 (FIG. 4) in this embodiment is to apply computer-assisted or computer-controlled image segmentation on a slice-by-slice basis with a view towards isolating an image of a fetal face from the volume image data received from the 2-D imager 40 (FIG. 4).

Following image segmentation, a volume image is constructed by volume constructor 45 (FIG. 4) and supplied to a 3-D sculpting tool 46 (FIG. 4), which is operative normally, but not necessarily, without operator intervention, to eliminate portions of the isolated image which occlude a desired image of a fetal face. Following operation of sculpting subsystem 42, a generally unoccluded image of the fetal face, with or without further image enhancement, is produced.

Figure 6:
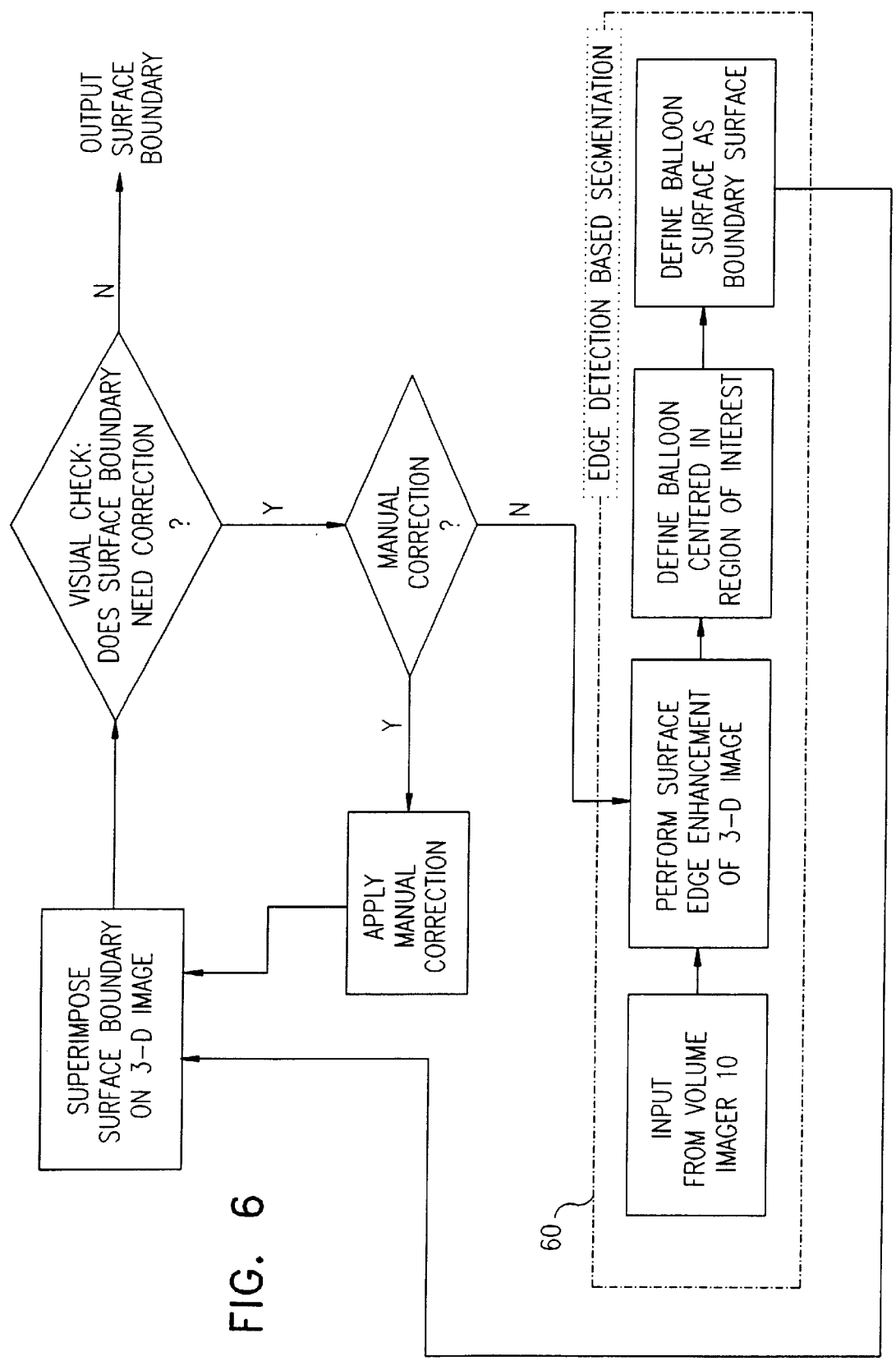
FIG. 6 is a flow chart illustrating 3-D image segmentation step of the operation of FIG. 5A in accordance with a preferred embodiment of the present invention.

Reference is now made to FIG. 6, which is a flow chart illustrating the 3-D image segmentation step of the operation of FIG. 5A in accordance with a preferred embodiment of the present invention.

As seen in FIG. 6, a 3-D image which may have associated therewith initial markings distinguishing between portions of the image which are of interest and portions of the image which it is desired to discard, is supplied to surface edge detection based segmentation circuitry 60 which preferably initially performs surface edge enhancement on the received 3-D image.

Following surface edge enhancement, a balloon is defined which is centered on a region of the image which is of interest. The balloon may be defined with the assistance of operator generated markings on the 3-D image, but does not require such markings.

The balloon may be subsequently automatically expanded or shrunk until its boundaries lie on or near enhanced edges of the 3-D image or on operator input markings, which may be supplied in the course of 3-D segmentation and not only prior thereto. The final balloon configuration defines one or more surface boundaries. An example of progressive shrinkage of the balloon about a fetal face is illustrated in FIGS. 8A, 8B, 8C and 8D. Shrinkage of the balloon is known from the following prior art publications, the disclosures of which are hereby incorporated by reference:

On Active Contour Models and Balloons, Laurent D. Cohen, CVGIP: IMAGE UNDERSTANDING, Vol. 53, No. 2, March, pp 211-218, 1991;

Finite-Element Methods for Active Contour Models and Balloons for 2-D and 3-D Images, Laurent D. Cohen and Isaac Cohen, IEEE TRANSACTIONS ON PATTERN ANALYSIS AND MACHINE INTELLIGENCE, Vol. 15, No. 11, November, 1993, pp 1131-1147;

Snakes, Active Contours, and Deformable Models http://www.wpi.edu/18dima/ummed/presentation/index.html.

The resultant one or more surface boundaries are superimposed on the 3-D image. An operator may carry out a visual confirmation check to satisfy himself that the indicated boundaries are indeed correct. If so, a closed surface boundary superimposed on the 3-D image is output.

Should the operator not be satisfied with the indicated surface boundary or boundaries he can carry out a manual correction or may additionally or alternatively have the boundaries recalculated by edge detection based segmentation circuitry 60. Whichever method is chosen, the corrected boundaries are superimposed on the 3-D image and a further visual check is conducted repeatedly until the operator is satisfied with the indicated boundaries.

Figure 7:
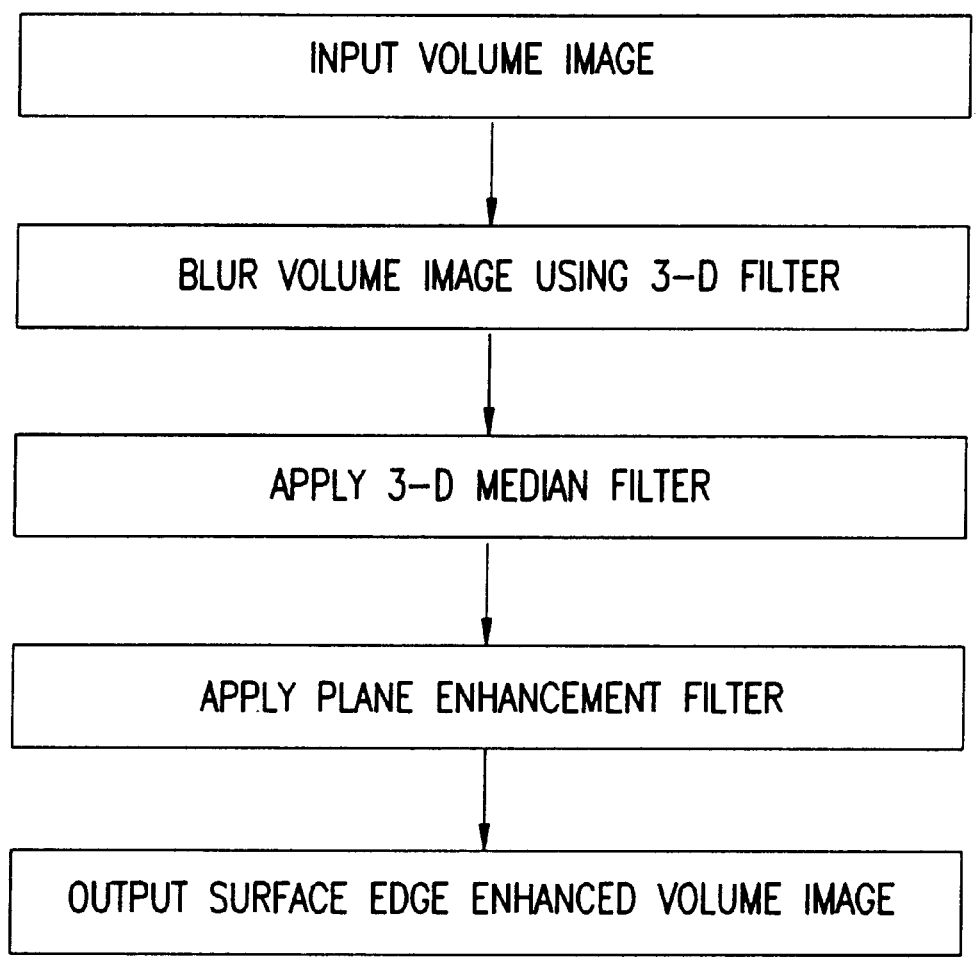
FIG. 7 is a flow chart illustrating a surface edge enhancement step of the operation of FIG. 6 in accordance with a preferred embodiment of the present invention.
Figure 8A:
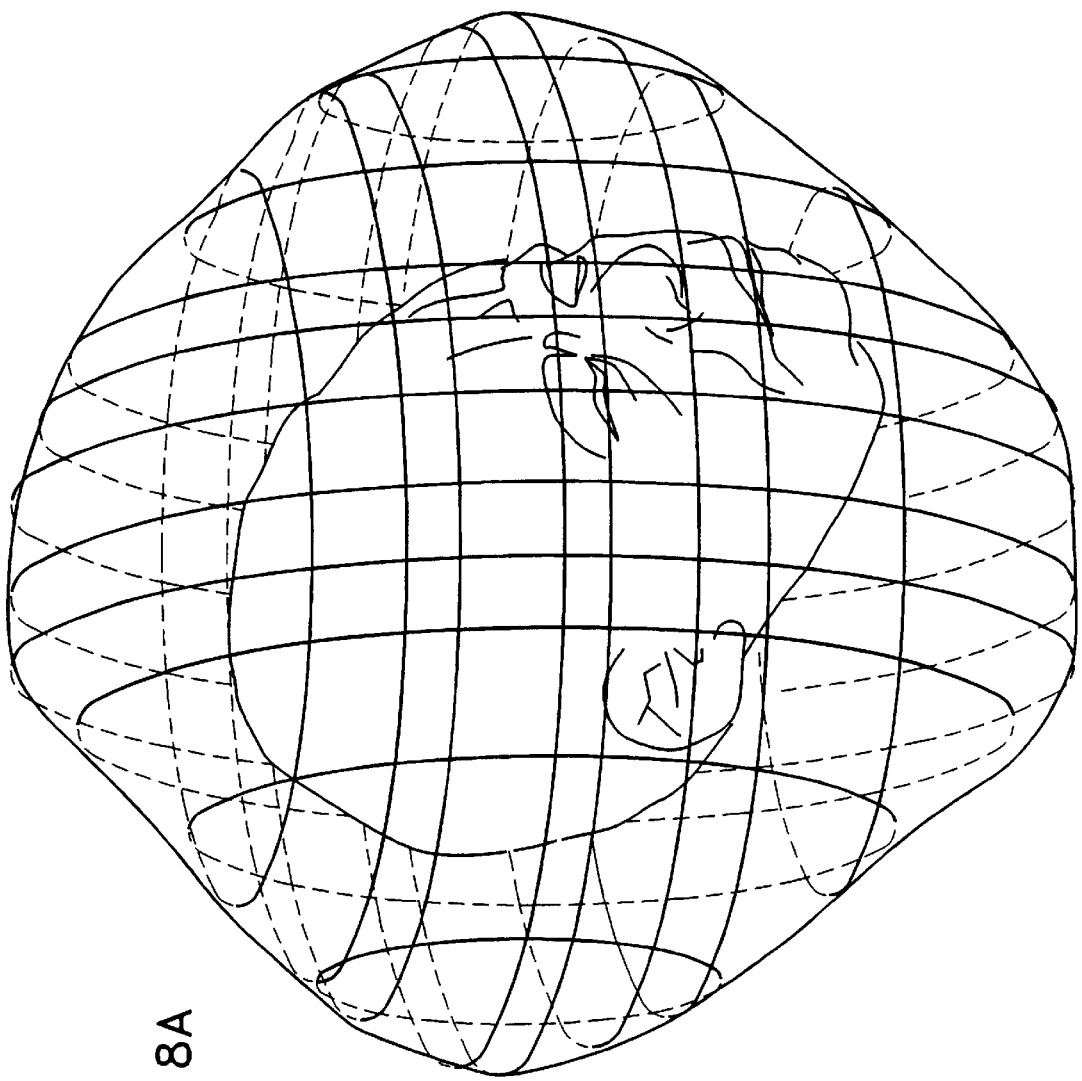
FIGS. 8A, 8B, 8C and 8D are pictorial illustrations showing the progressive shrinking of an imaging balloon about an image of the head of a fetus.
Figure 8B:
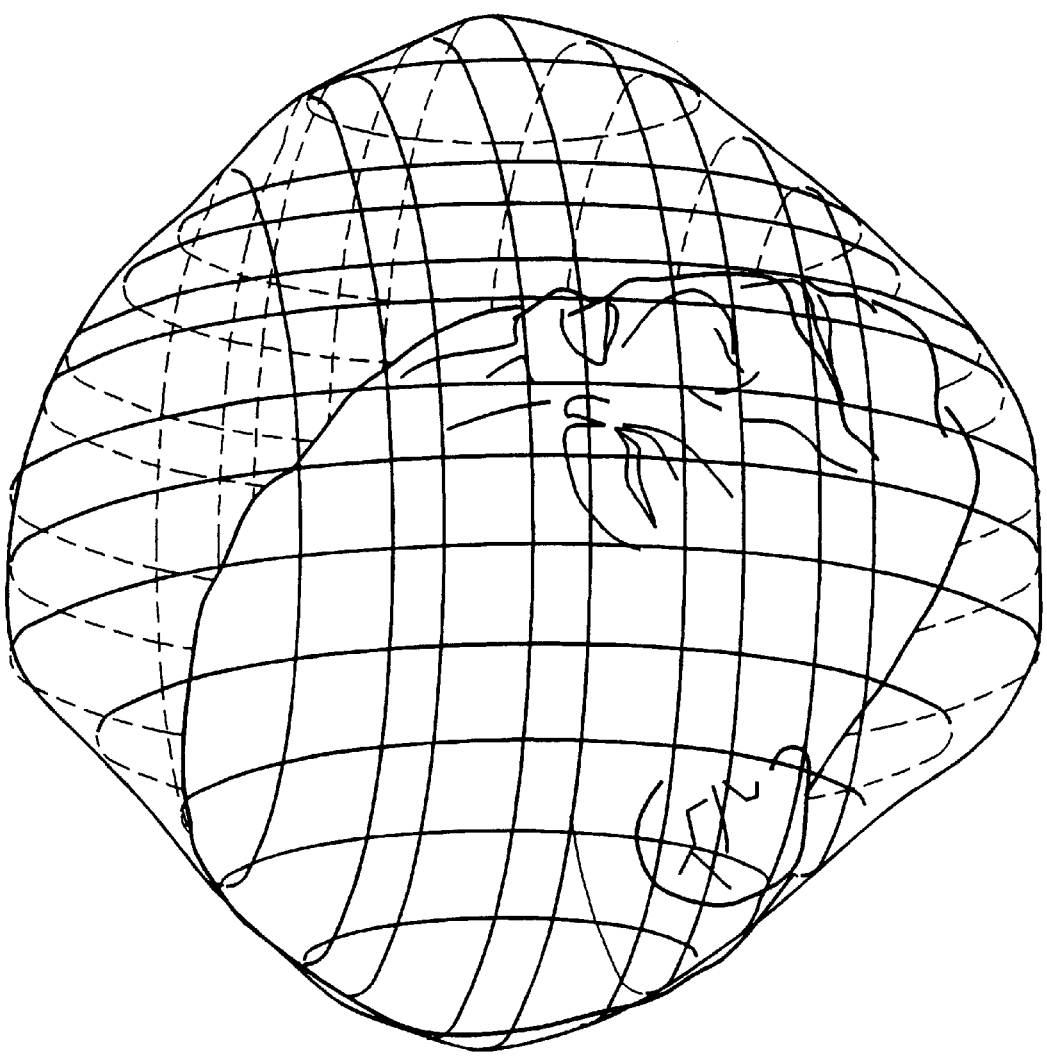
Figure 8C:
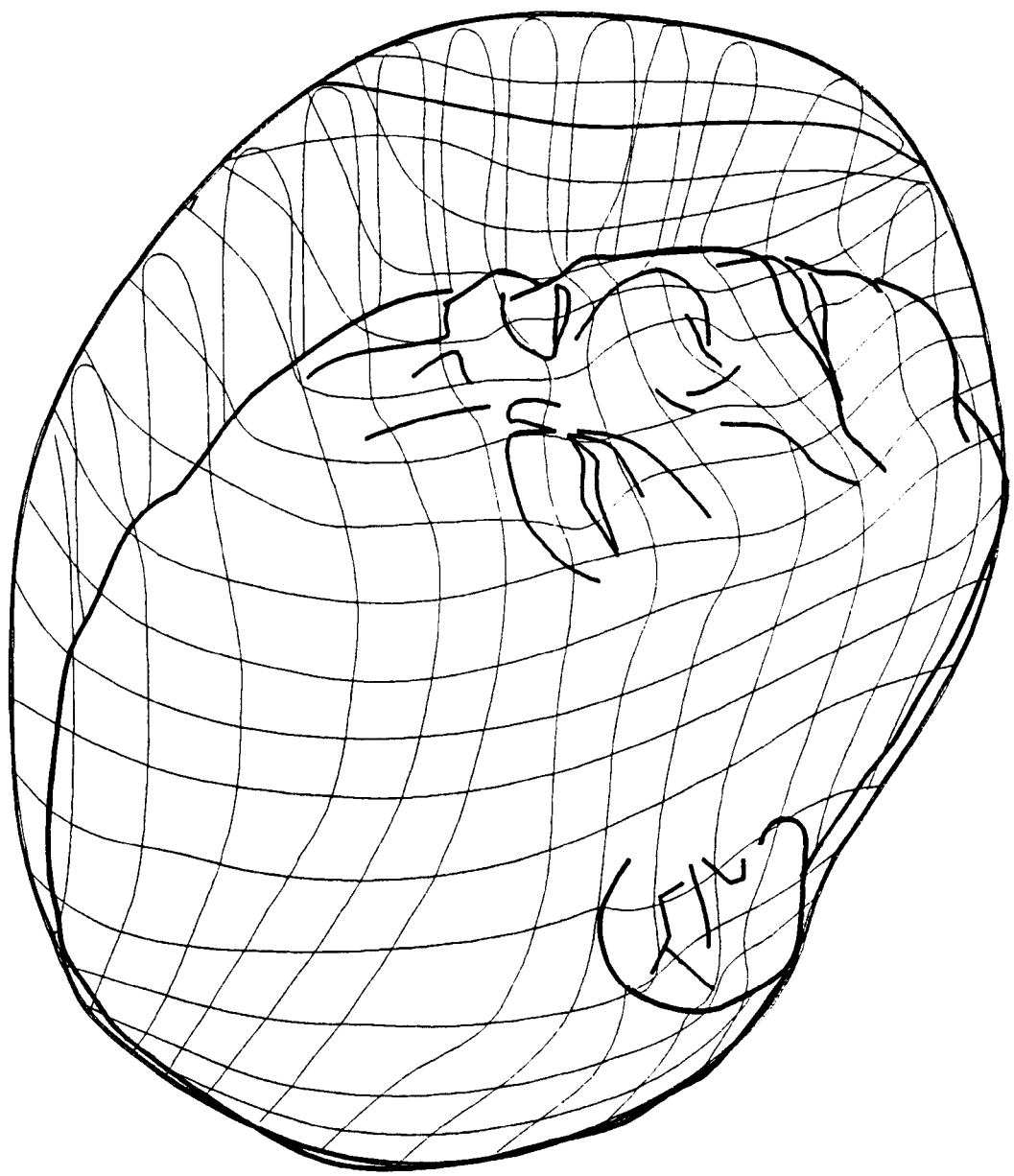
Figure 8D:
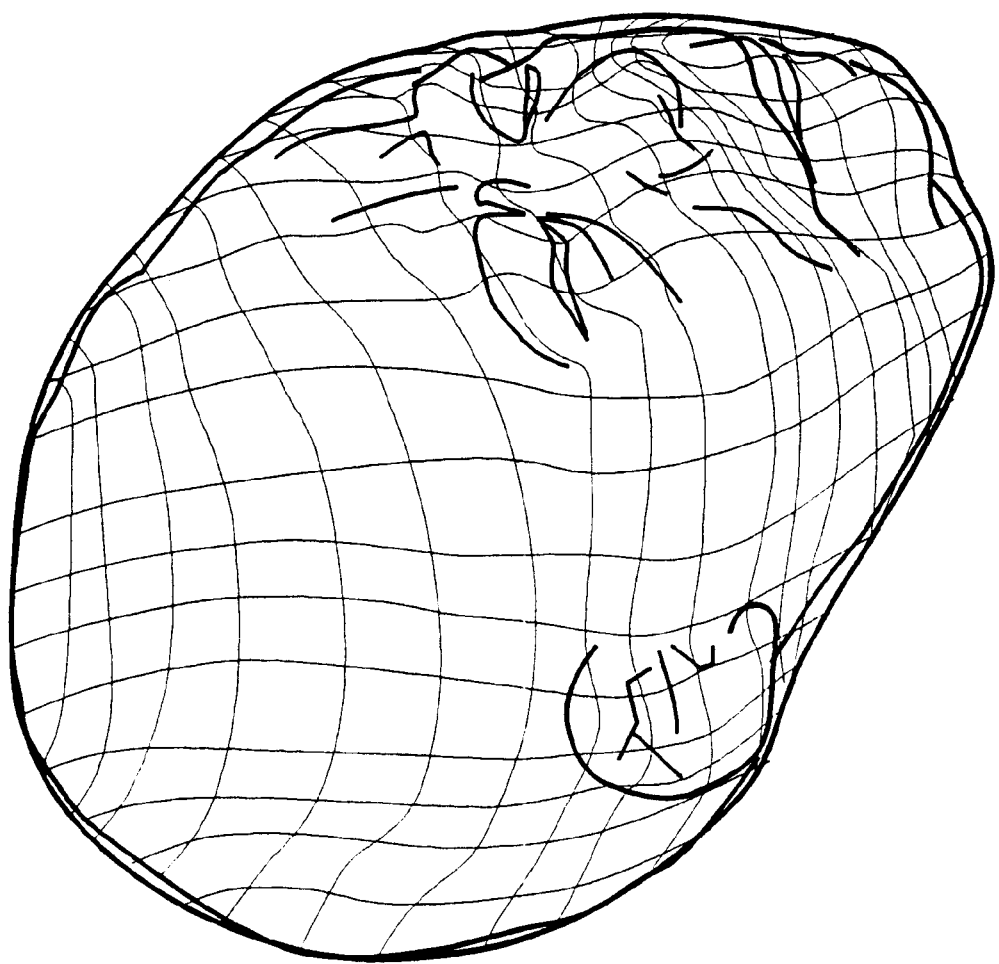

Reference is now made to FIG. 7, which is a flow chart illustrating a surface edge enhancement step of the operation of FIG. 6 in accordance with a preferred embodiment of the present invention. As seen in FIG. 7, following input of the volume image from volume imager 10, the volume image is preferably blurred using a 3-D filter, such as a 3-D Gaussian filter. Thereafter, a 3-D median filter is preferably applied to the blurred volume image. The preceding two steps are examples of noise suppression techniques useful in edge enhancement pre-processing.

Following the noise suppression steps described above, a plane enhancement filter is applied to the pre-processed image, thus producing a surface edge enhanced volume image output.

Figure 9B:
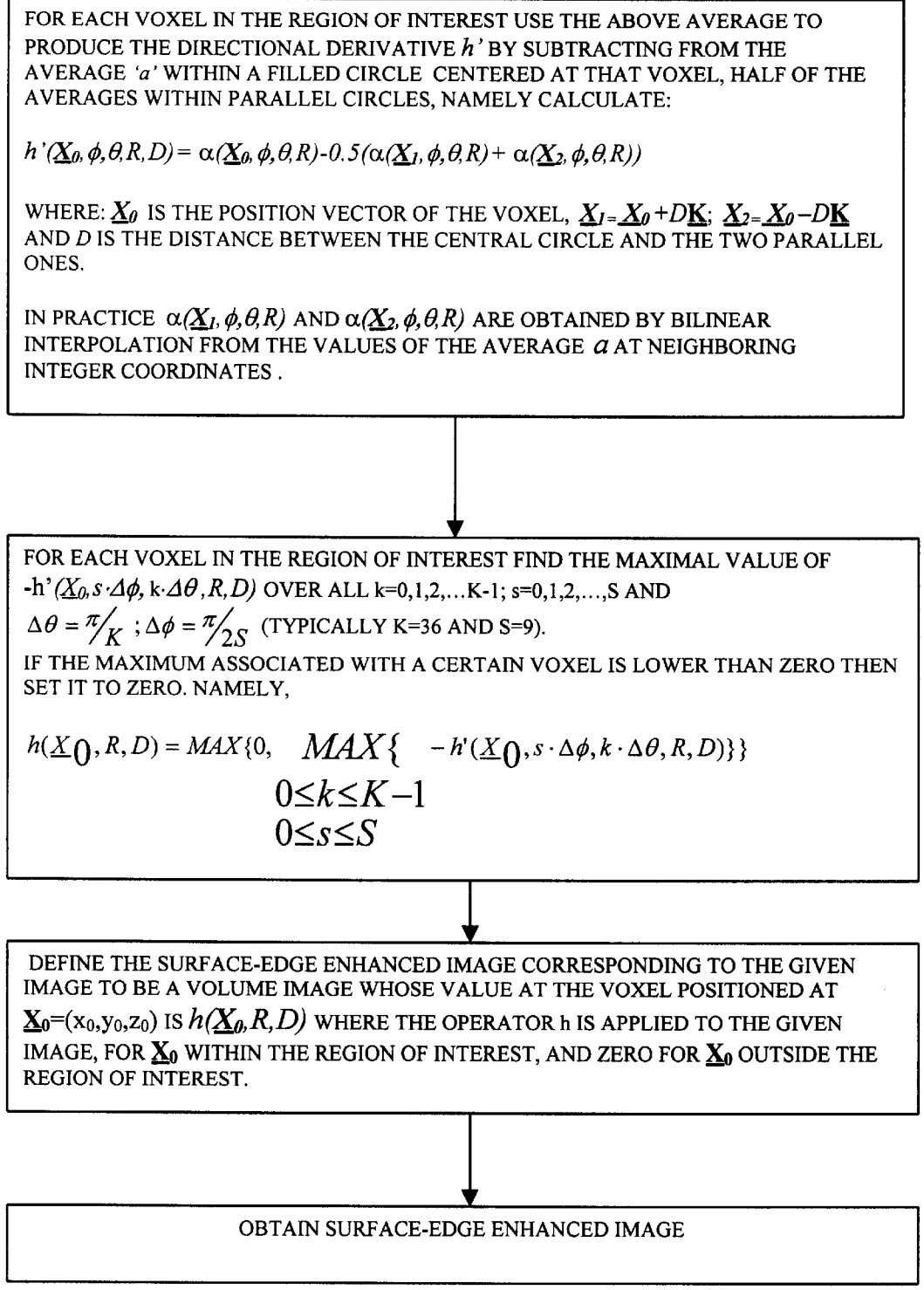
Figure 10:
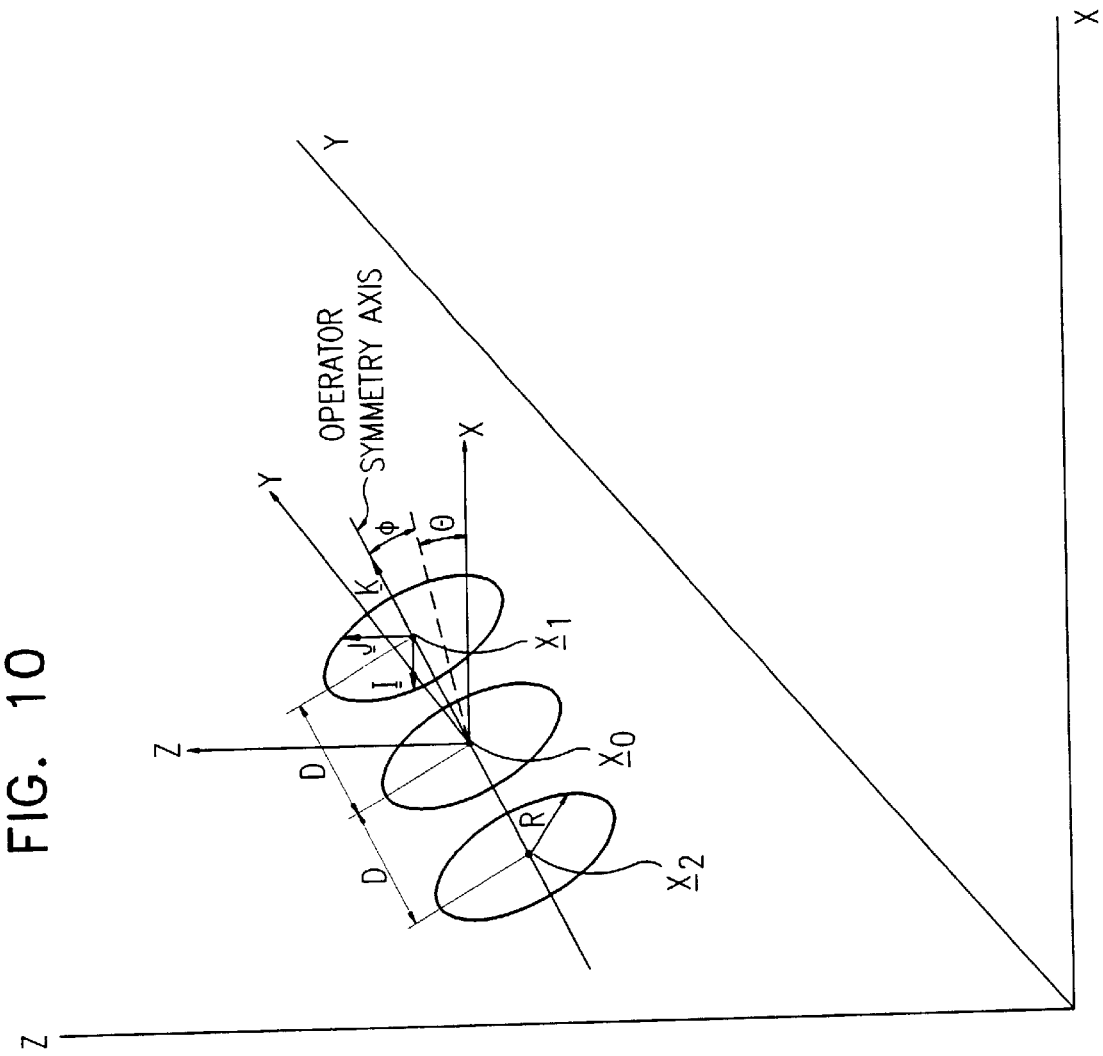
FIG. 10 is an illustration useful in understanding the filtering operation illustrated in FIGS. 9A and 9B.

Reference is now made to FIGS. 9A and 9B, which together are a flowchart illustrating a three-dimensional filtering operation performed in accordance with a preferred embodiment of the present invention on an original volume image. Such a filtering operation is preferably employed as part of the step of performing surface edge enhancement of a 3-D image forming part of edge detection based segmentation 60, as shown in FIG. 6, and corresponds to the step in FIG. 7 identified as "APPLY PLANE ENHANCEMENT FILTER". Reference is also made in this context to FIG. 10, which is an illustration useful in understanding the filtering operation illustrated in FIGS. 9A and 9B;

FIGS. 9A and 9B taken together with FIG. 10, describe steps of a filtering operation which is performed on the volume image received from volume imager 10 in accordance with a preferred embodiment of the present invention. The detailed flowchart of FIGS. 9A and 9B describes a plane enhancement operator. The plane enhancement operator is an extension to three dimensions of edge or ridge enhancement operators in 2 dimensions described hereinbelow with reference to FIGS. 13A & 13B as well as FIG. 17.

The plane enhancement operator operates upon a volumetric image and provides a grey-level volumetric image output in which the edges or ridges appear as enhanced surfaces in three dimensions. Stated more generally, the operator provides a volumetric image representation of the intensity of the surface edge property at each image voxel. FIG. 10 is an illustration of the plane enhancement operator whose functionality is detailed in FIGS. 9A & 9B. For the sake of conciseness, in view of the detailed nature of the steps of the operation indicated in FIGS. 9A and 9B with reference to FIG. 10, a further textual explanation of these steps is believed to be unnecessary and thus is not provided.

Figure 11:
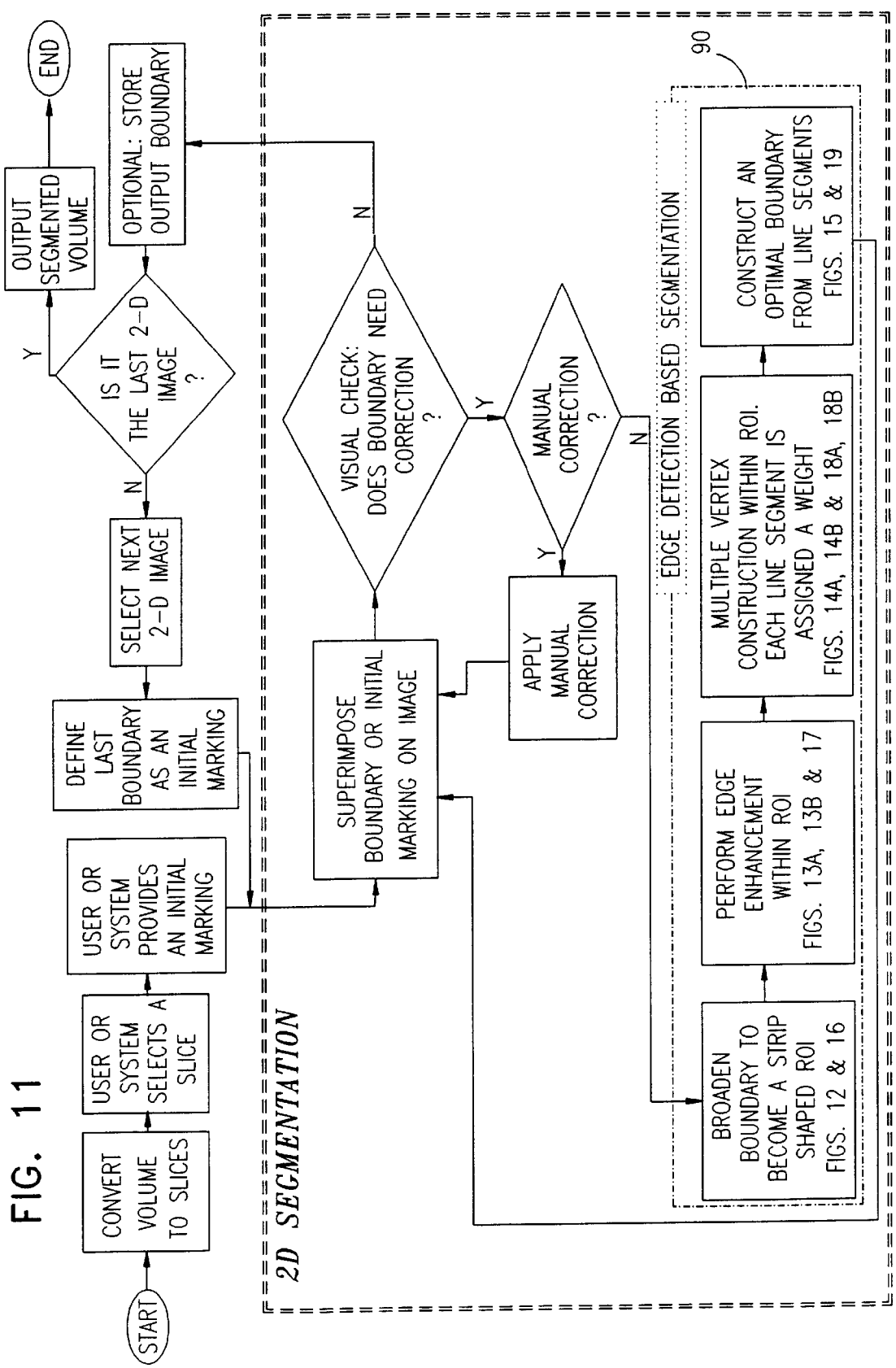
FIG. 11 is a flow chart illustrating 3-D image segmentation step of the operation of FIG. 5B in accordance with a preferred embodiment of the present invention.

Reference is now made to FIG. 11, which is a flow chart illustrating a 3-D image segmentation step of the operation of FIG. 5B in accordance with a preferred embodiment of the present invention. FIG. 11 presents details of slice by slice segmentation in the operation of FIG. 5B. As seen in FIG. 11, a 2-D image, which may be sliced from a volume image, is selected by the system or by an operator and is initially operated on by the segmenter using an operator input which applies initial markings, such as boundary markings, to various portions of the 2-D image to distinguish between portions of the image which are of interest and portions of the image which it is desired to discard.

Thereafter, fully or partially computerized 2-D segmentation is carried out using edge detection techniques in accordance with an algorithm which is described hereinbelow. The segmenter provides an output which may be stored while additional 2-D image slices are segmented as described hereinabove.

For each subsequent 2-D image, the output and/or other characteristics of at least one preceding 2-D image are used as initial markings or in any other suitable manner for determining or partially determining the boundary. It is appreciated that the image may include more than one boundary. Once all of the required 2-D images have been segmented, a segmentation output is provided to the sculpting tool.

The segmentation output defines a closed boundary or boundaries distinguishing portions of the image which are of interest and portions of the image which it is desired to discard.

The 2-D segmentation step shown in FIG. 11 preferably incorporates the following steps:

Initial markings or the preceding boundary are superimposed on the image and a visual check of the boundary may then be carried out. If the boundary appears to need correction and a manual correction is called for, a manual correction is carried out. If, however the boundary does not appear to need correction, it is preferably stored. If the slice being segmented is the last 2-D image slice to be segmented in the 3-D image, the volume having the output boundary or boundaries superimposed thereover is output. If the slice being segmented is not the last 2-D slice to be segmented in the 3-D image, a further 2-D slice is selected. The previous boundary is preferably defined as an initial boundary for the further slice.

If, however, the boundary or boundaries are found to need correction and manual correction is selected, a manual correction module applies a manual correction to the boundary or boundaries superimposed on the image. If manual correction is not called for, computerized correction is typically effected by edge detection based segmentation circuitry 90.

Figure 18A:
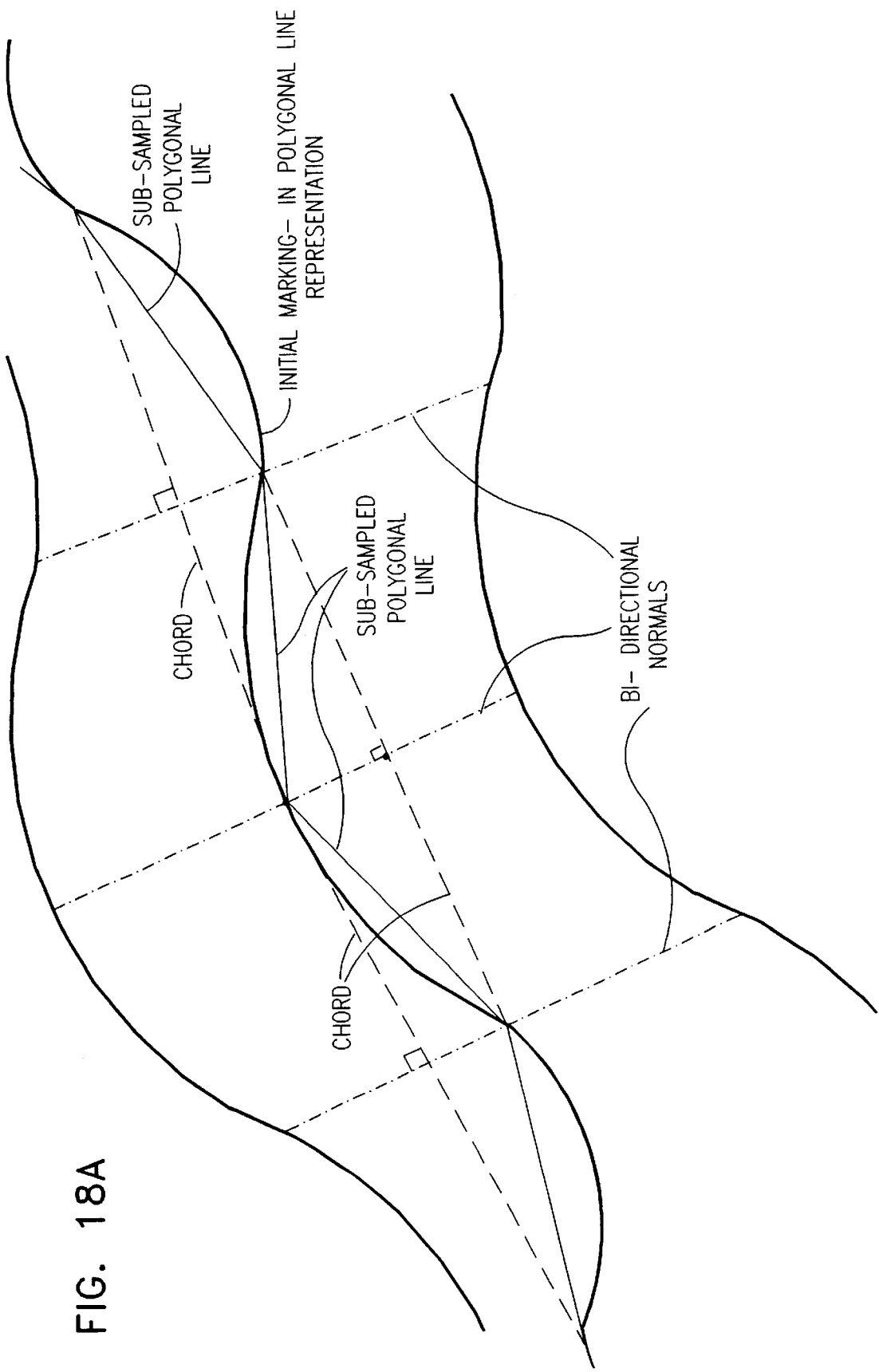
FIGS. 18A and 18B are illustrations useful in understanding the flowchart of FIGS. 14A and 14B.
Figure 18B:
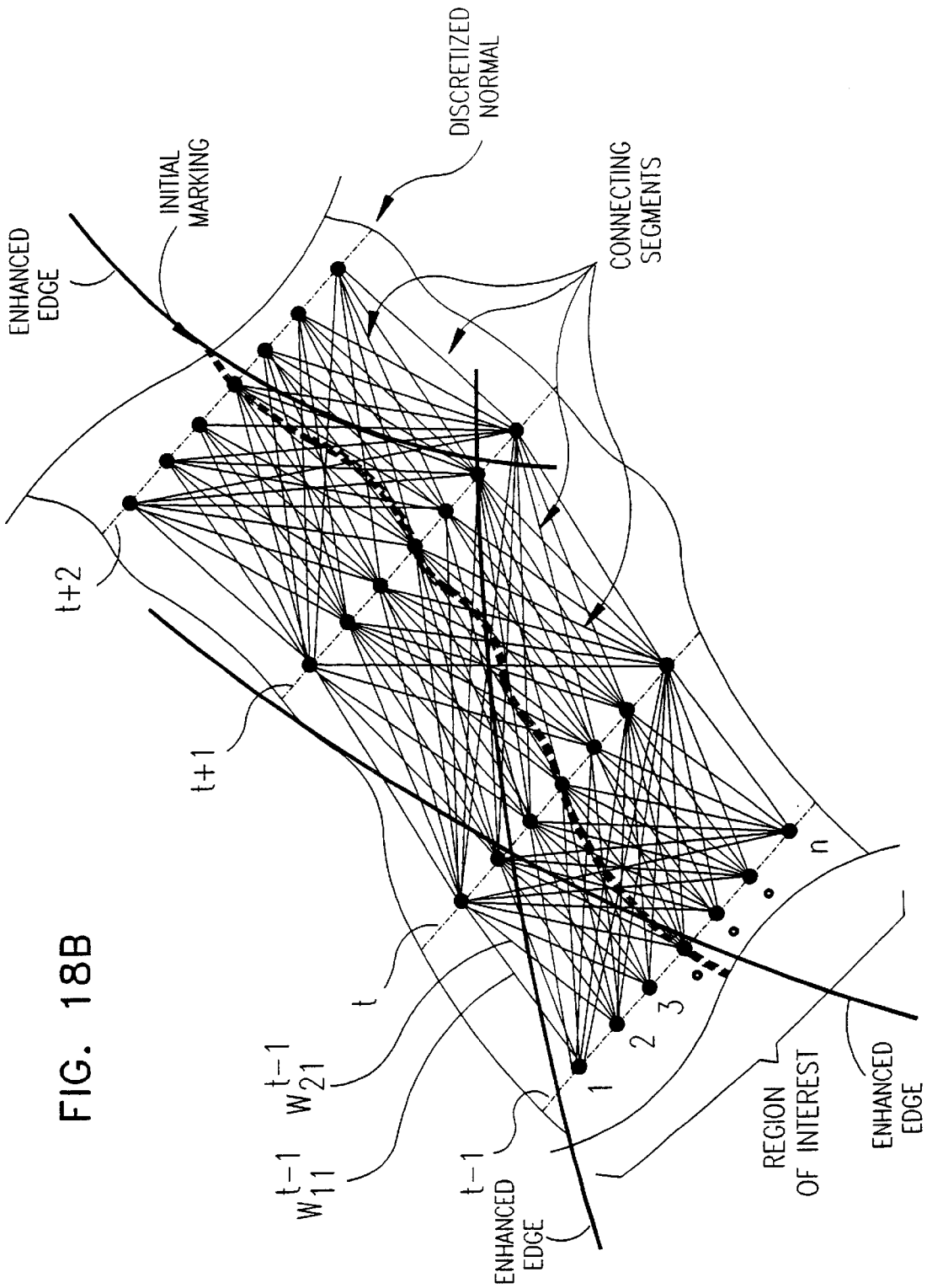

The operation of edge detection based segmentation circuitry 90 may be summarized as follows: The boundary or boundaries initially superimposed on the image are supplied to circuitry 90 separately from the image and are broadened in order to define a strip-shaped region or regions of interest (ROI). Edge enhancement is performed on the image, preferably, but not necessarily, within the ROI. As seen in FIGS. 18A & 18B, referred to hereinbelow, a multiple vertex geometrical construction is provided within the region of interest and includes a multiplicity of vertices interconnected by line segments, wherein each line segment is assigned a weight. As described in greater detail hereinbelow, an optimal boundary is constructed from the line segments. The optimal boundary is then superimposed onto the image.

The foregoing segmentation method continues until it is decided that the boundary on the last 2-D image of the volume does not require correction.

Figure 12:
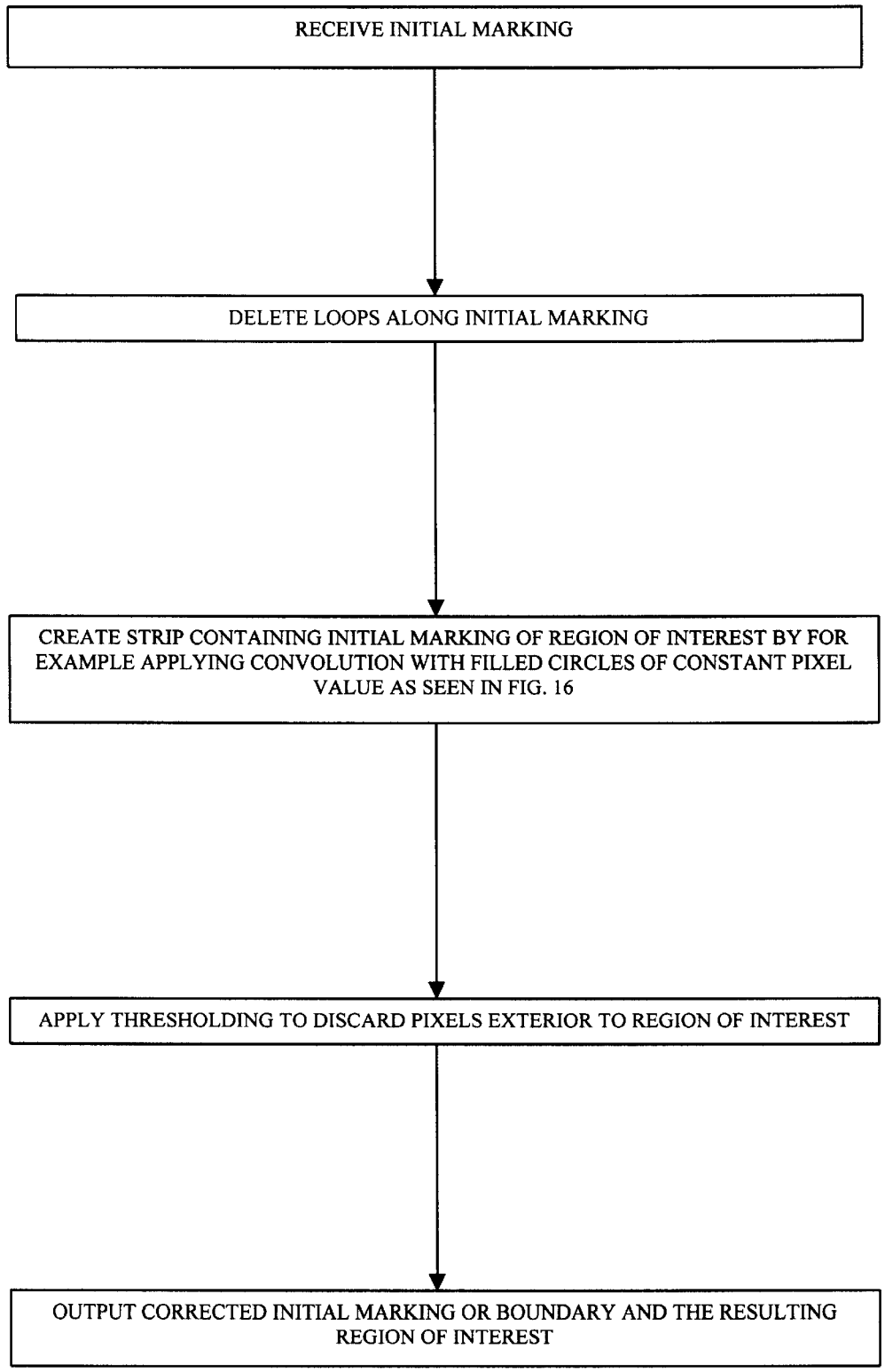
FIG. 12 is a flow chart illustrating a region of interest defining step of the operation of FIG. 11 in accordance with a preferred embodiment of the present invention.
Figure 16:
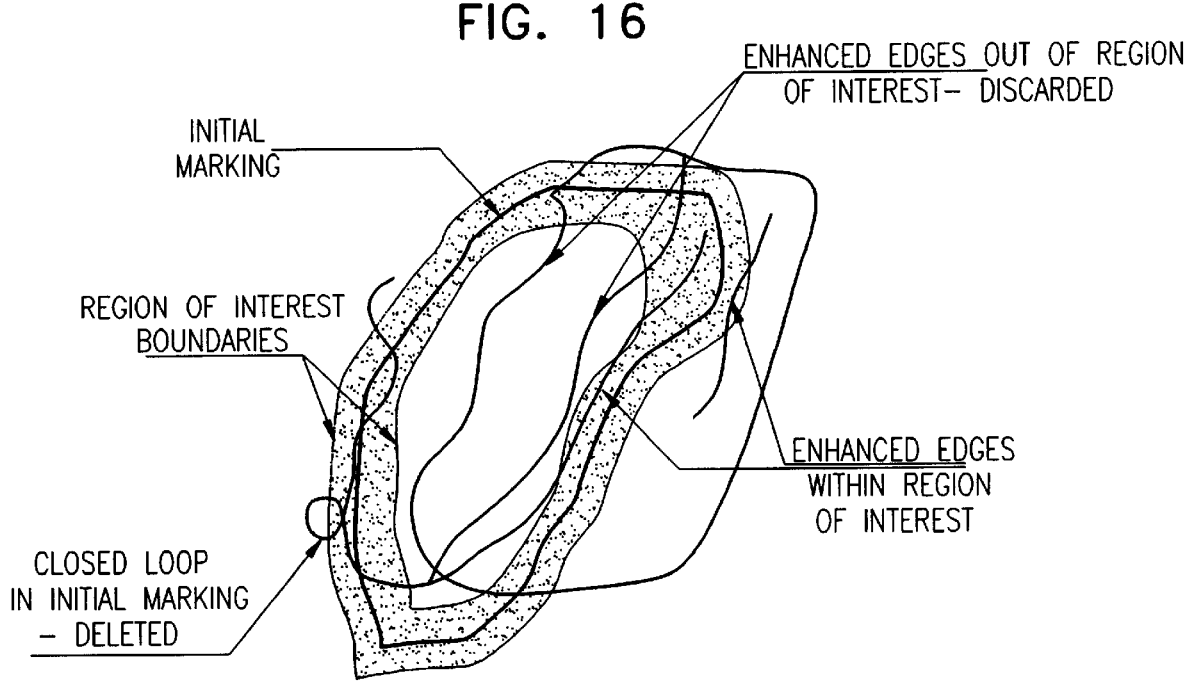
FIG. 16 is an illustration useful in understanding the flowchart of FIG. 12.

Reference is now made to FIG. 12, which is a flow chart illustrating a strip-shaped region of interest defining step of the operation of FIG. 11 in accordance with a preferred embodiment of the present invention and to FIG. 16 which shows such a region of interest.

As seen in FIG. 12, the initial marking or boundary is received and any closed loops, as illustrated in FIG. 16, along the initial marking or boundary are deleted. A strip-shaped region of interest is defined about each initial marking or boundary, for example by employing a convolution having filled circles of constant pixel value as a convolution kernel. The circles need not all have the same diameter. A thresholding function is then applied to discard pixels located exteriorly to the region of interest. The thus-corrected initial marking or boundary is then output together with the strip-shaped region of interest.

Figure 17:
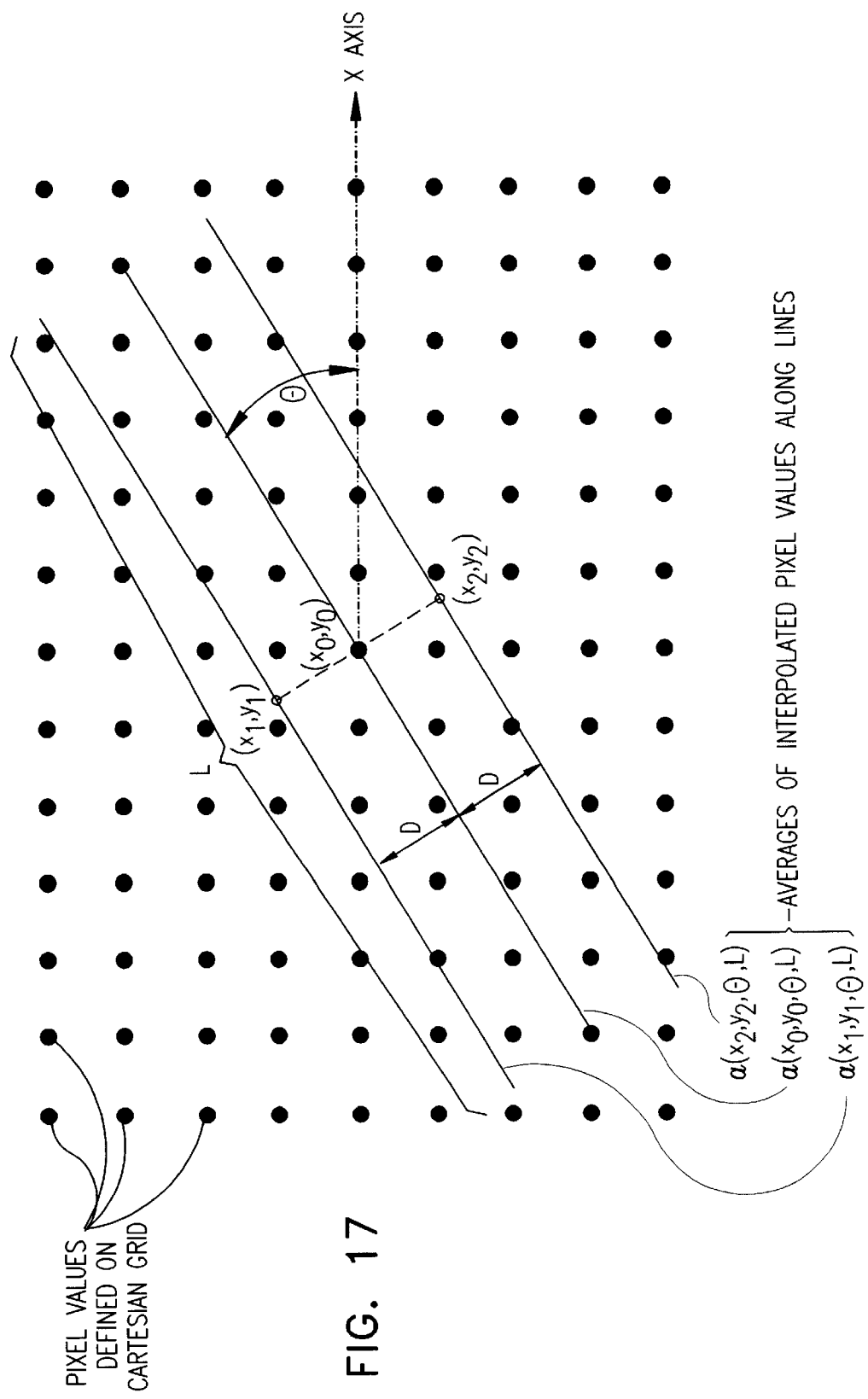
FIG. 17 is an illustration useful in understanding the flowchart of FIGS. 13A and 13B.

Reference is now made to FIGS. 13A and 13B, which together are a flowchart illustrating a two-dimensional edge enhancement filtering operation performed in accordance with a preferred embodiment of the present invention on a slice of the original volume image and to FIG. 17, which is an illustration useful in understanding the flowchart of FIGS. 13A and 13B. It is appreciated that the operation of FIGS. 13A and 13B provides a grey level edge enhanced image. Stated more generally, the operation provides an image representation of the intensity of the edge property at each image pixel.

The operation illustrated in FIGS. 13A, 13B and 17 is carried out at each pixel location in each slice of the volume image and searches for a candidate edge segment at every such pixel location, preferably by searching for the direction of a candidate edge segment. For the sake of conciseness, in view of the detailed nature of the steps of the operation indicated in FIGS. 13A and 13B with reference to FIG. 17, a further textual explanation of these steps is believed to be unnecessary and thus is not provided.

Figure 14A:
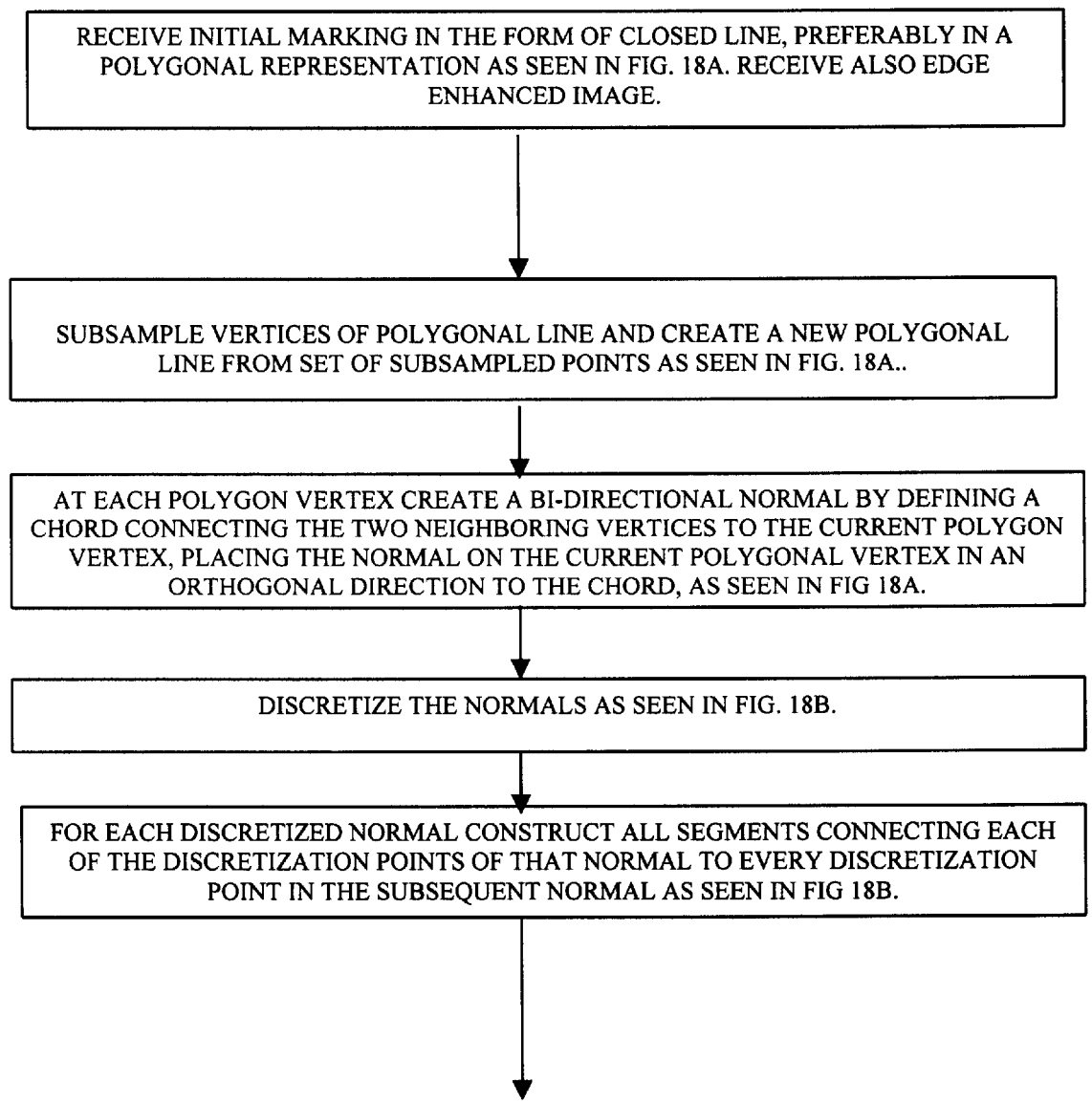

Reference is now made to FIGS. 14A and 14B, which together are a flow chart illustrating one part of an optimal boundary defining step of the operation of FIG. 11 in accordance with a preferred embodiment of the present invention which includes providing a multiple vertex geometrical construction within the region of interest having a multiplicity of vertices interconnected by line segments, wherein each line segment is assigned a weight.

Reference is also made to FIGS. 18A and 18B, which are useful in the understanding of the flow chart of FIGS. 14A & 14B. The functionality of FIGS. 14A & 14B provides information for use in defining a closed boundary within the region of interest. The closed boundary is determined at each point therealong inter alia based on the following characteristics: proximity to an initial marking or a boundary already determined for an adjacent or other slice, the degree of similarity in direction to the initial marking or previously determined boundary and the degree of overlap with the initial marking or previously determined boundary.

Optionally, not only the configuration of the previously determined boundary for another slice or other slices, but also some or all of the above-listed characteristics of the said slice or slices, may be employed in subsequently determining the boundary for the current slice.

For the sake of conciseness, in view of the detailed nature of the steps of the operation indicated in FIGS. 14A and 14B with reference to FIGS. 18A and 18B, a further textual explanation of these steps is believed to be unnecessary and thus is not provided.

Figure 15:
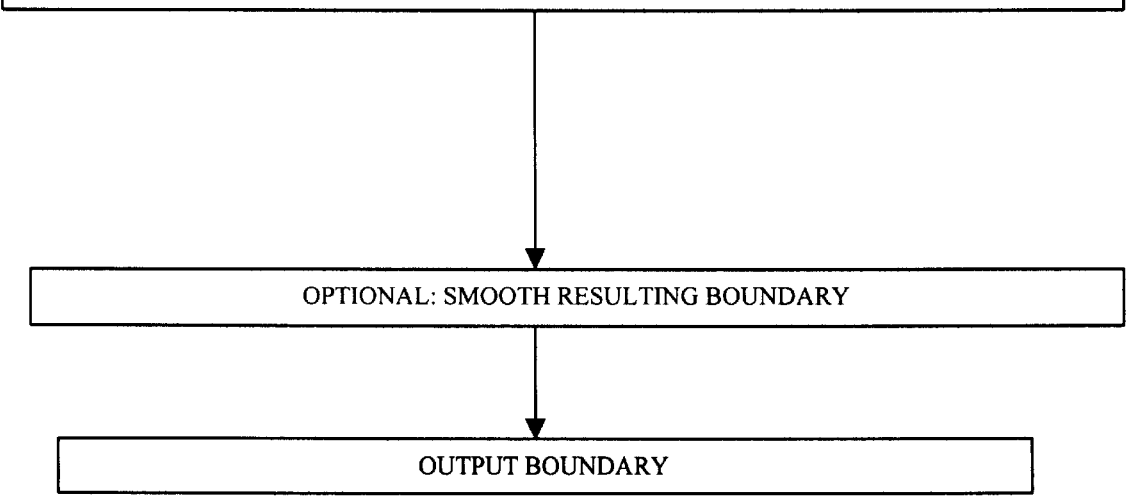
FIG. 15 is a flow chart illustrating another part of the optimal boundary defining step of the operation of FIG. 11 in accordance with a preferred embodiment of the present invention.
Figure 19:
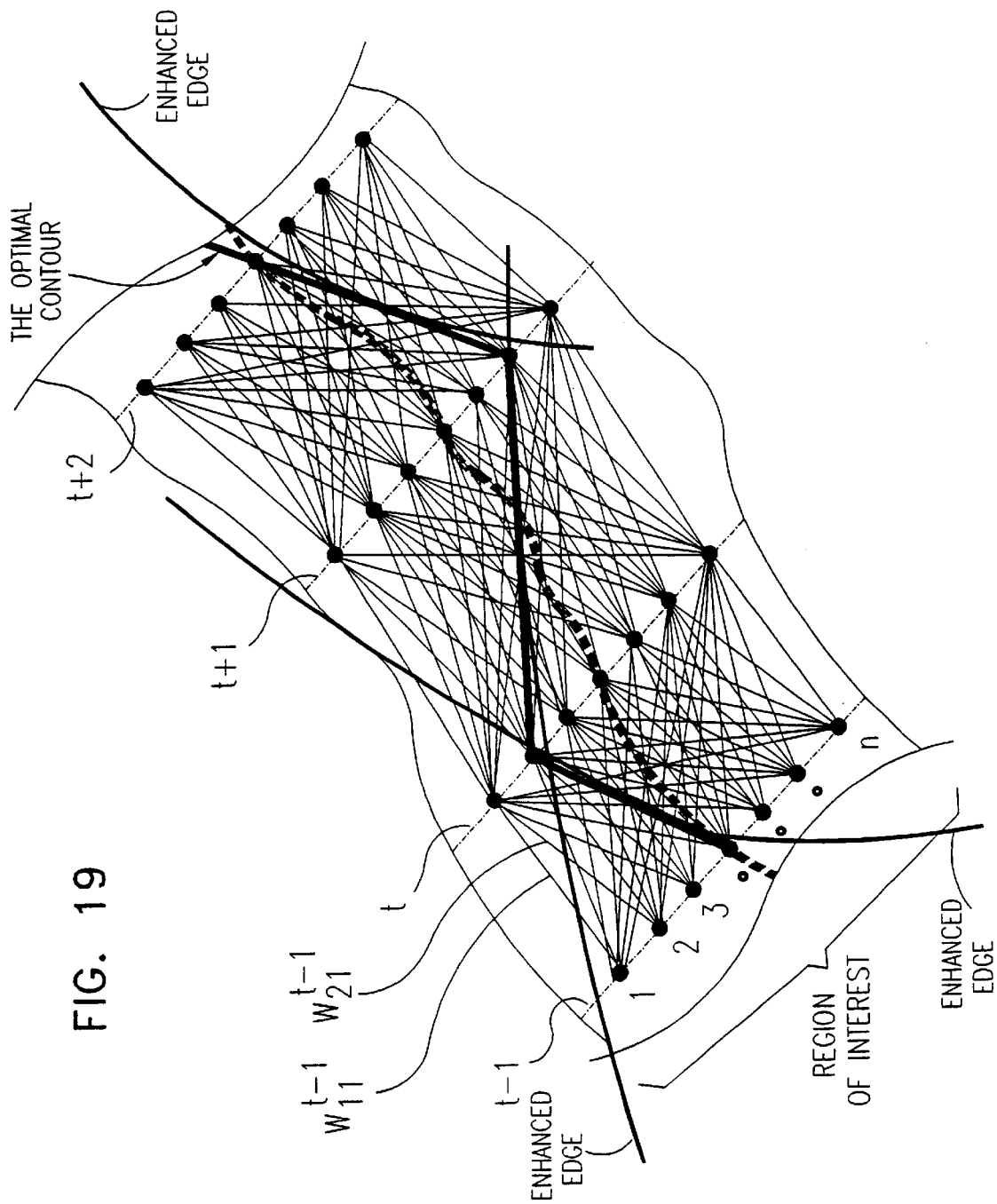
FIG. 19 is an illustration useful in understanding the flowchart of FIG. 15.

Reference is now made to FIG. 15, which is a flow chart illustrating a further part of the optimal boundary defining step of the operation of FIG. 11 in accordance with a preferred embodiment of the present invention which provides an optimal boundary by employing dynamic programming based on the operations described hereinabove with reference to FIGS. 14A, 14B, 18A and 18B. Reference is also made to FIG. 19, which is an illustration useful in understanding the flowchart of FIG. 15.

Figures 20A, 20B:
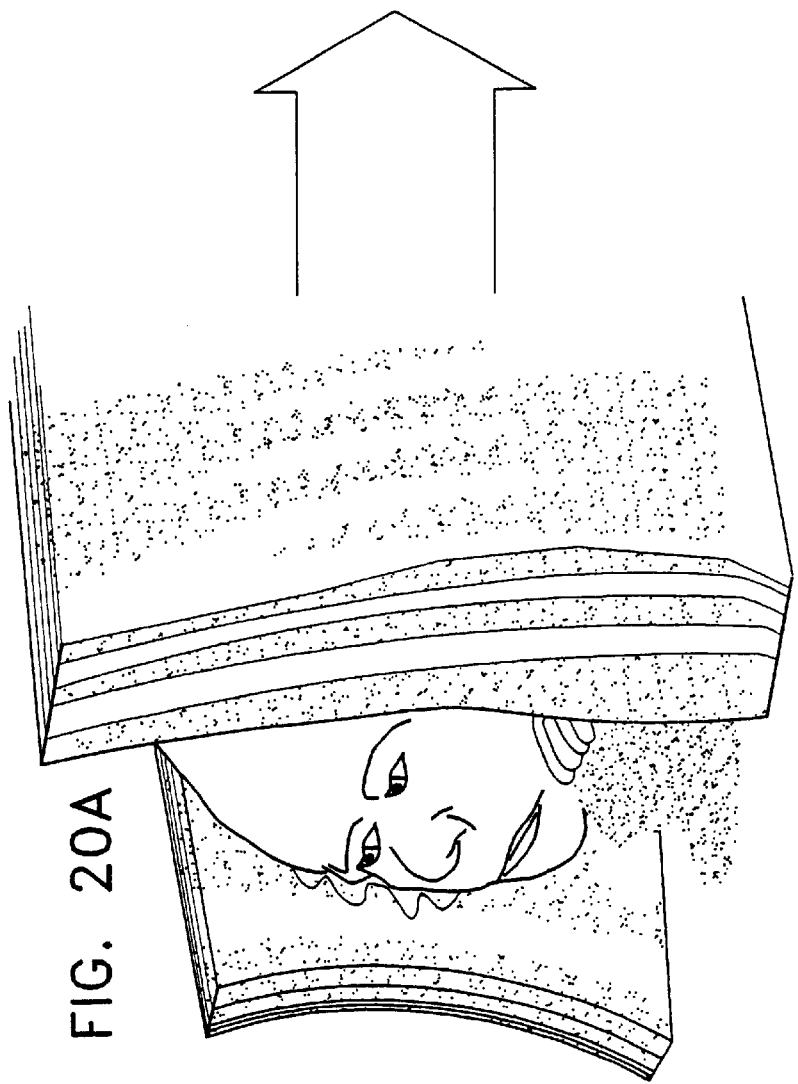
FIGS. 20A and 20B are simplified illustrations showing operation of a preferred embodiment of the present invention.

The overall operation of the present invention may be understood from a consideration of FIGS. 20A and 20B. FIG. 20A schematically depicts the head of a fetus partially occluded by the uterus and placenta. The operation of the present invention provides an image of the head of the fetus without such occlusions (FIG. 20B).

It will be appreciated by persons skilled in the art that the present invention is not limited to what has been particularly shown and described hereinabove. Rather the scope of the present invention includes both combinations and subcombinations of various elements described hereinabove as well as modifications and variations thereof which would occur to a person skilled in the art upon reading the foregoing description and which are not in the prior art.

What is claimed is:

1. A system for providing an image of at least a portion of a fetus in utero comprising:
   an imager providing image data for a volume including at least a portion of a fetus in utero;
   an at least partially computer controlled image processing algorithm based segmenter for defining geometrical boundaries of various objects in said volume as well as including said at least a portion of a fetus in utero; and
   a sculpting tool, utilizing the geometrical boundaries of at least some of said various objects defined by said segmenter, for selectably removing image data relating to at least portions of said objects in order to provide a desired non-occluded image of said at least a portion of said fetus in utero based on said image data.

2. A system for providing an image of at least a portion of a fetus in utero according to claim 1 and wherein said imager is an ultrasound imager.

3. A system for providing an image of at least a portion of a fetus in utero according to claim 1 and wherein said image data contains speckles.

4. A system for providing an image of at least a portion of a fetus in utero according to claim 2 and wherein said image data contains speckles.

5. A system for providing an image of at least a portion of a fetus in utero according to claim 1 and wherein said segmenter is fully automatic.

6. A system for providing an image of at least a portion of a fetus in utero according to claim 1 and wherein said segmenter is semi-automatic.

7. A system for providing an image of at least a portion of a fetus in utero according to claim 1 and wherein said segmenter operates substantially in real time.

8. A system for providing an image of at least a portion of a fetus in utero according to claim 1 and wherein said segmenter defines geometrical boundaries in at least one slice of said volume by employing previously acquired information relating to at least another slice of said volume.

9. A system for providing an image of at least a portion of a fetus in utero according to claim 2 and wherein said segmenter defines geometrical boundaries in at least one slice of said volume by employing previously acquired information relating to at least another slice of said volume.

10. A system for providing an image of at least a portion of a fetus in utero according to claim 1 and wherein said segmenter operates in a slice-by-slice manner.

11. A method for providing an image of at least a portion of a fetus in utero comprising the steps of:
    providing image data for a volume including at least a portion of a fetus in utero;
    utilizing an at least partially computer controlled image processing algorithm based segmenter to define geometrical boundaries of various objects in said volume as well as including said at least a portion of a fetus in utero; and
    utilizing the geometrical boundaries of at least some of said various objects defined by said segmenter to selectably remove image data relating to at least portions of said objects in order to provide a desired non-occluded image of said at least a portion of said fetus in utero based on said image data.

12. A method for providing an image of at least a portion of a fetus in utero according to claim 11 and wherein said imager employs ultrasound.

13. A method for providing an image of at least a portion of a fetus in utero according to claim 11 and wherein said image data contains speckles.

14. A method for providing an image of at least a portion of a fetus in utero according to claim 12 and wherein said image data contains speckles.

15. A method for providing an image of at least a portion of a fetus in utero according to claim 11 and wherein said segmenter operates fully automatically.

16. A method for providing an image of at least a portion of a fetus in utero according to claim 11 and wherein said segmenter operates semi-automatically.

17. A method for providing an image of at least a portion of a fetus in utero according to claim 11 and wherein said segmenter operates substantially in real time.

18. A method for providing an image of at least a portion of a fetus in utero according to claim 11 and wherein said segmenter defines geometrical boundaries in at least one slice of said volume by employing previously acquired information relating to at least another slice of said volume.

19. A method for providing an image of at least a portion of a fetus in utero according to claim 12 and wherein said segmenter defines geometrical boundaries in at least one slice of said volume by employing previously acquired information relating to at least another slice of said volume.

20. A method for providing an image of at least a portion of a fetus in utero according to claim 11 and wherein said segmenter operates in a slice-by-slice manner.

* * * * *